(12) United States Patent
Ferrari et al.

(10) Patent No.: US 10,253,424 B2
(45) Date of Patent: *Apr. 9, 2019

(54) POROUS PARTICLES AND METHODS OF MAKING THEREOF

(71) Applicants: Board of Regents of the University of Texas System, Austin, TX (US); The Ohio State University Research Foundation, Columbus, OH (US)

(72) Inventors: Mauro Ferrari, Houston, TX (US); Xuewu Liu, Sugar Land, TX (US); Ming-Cheng Cheng, Pearland, TX (US)

(73) Assignees: BOARD OF REGENTS OF THE UNIVERSITY OF TEXAS SYSTEM, Austin, TX (US); THE OHIO STATE UNIVERSITY RESEARCH FOUNDATION, Columbus, OH (US)

( * ) Notice: Subject to any disclaimer, the term of this patent is extended or adjusted under 35 U.S.C. 154(b) by 488 days.

This patent is subject to a terminal disclaimer.

(21) Appl. No.: 14/538,065

(22) Filed: Nov. 11, 2014

(65) Prior Publication Data
US 2016/0032480 A1   Feb. 4, 2016

Related U.S. Application Data

(63) Continuation of application No. 12/110,515, filed on Apr. 28, 2008, now Pat. No. 8,920,625, which is a (Continued)

(51) Int. Cl.
*A61K 9/14* (2006.01)
*C25F 3/12* (2006.01)
(Continued)

(52) U.S. Cl.
CPC ............... *C25F 3/12* (2013.01); *A61K 8/25* (2013.01); *A61K 9/141* (2013.01); *C01B 33/02* (2013.01);
(Continued)

(58) Field of Classification Search
None
See application file for complete search history.

(56) References Cited

U.S. PATENT DOCUMENTS 6,099,864 A    8/2000 Morrison et al.
6,107,102 A    8/2000 Ferrari
(Continued)

FOREIGN PATENT DOCUMENTS

CN    1939585    4/2007
EP    0466986    4/1994
(Continued)

OTHER PUBLICATIONS

Akerman et al., "Nanocrystal targeting in vivo," Proc. Natl. Acad. Sci. USA, Oct. 1, 2002, 99(20):12617-12621.
(Continued)

*Primary Examiner* — Paul S Hyun
(74) *Attorney, Agent, or Firm* — Winstead PC

(57) ABSTRACT

Provided is a particle that includes a first porous region and a second porous region that differs from the first porous region. Also provided is a particle that has a wet etched porous region and that does have a nucleation layer associated with wet etching. Methods of making porous particles are also provided.

24 Claims, 16 Drawing Sheets

Related U.S. Application Data continuation-in-part of application No. 11/836,004, filed on Aug. 8, 2007, now abandoned.

(60) Provisional application No. 60/914,358, filed on Apr. 27, 2007, provisional application No. 60/914,348, filed on Apr. 27, 2007.

(51) Int. Cl.
*A61K 8/25* (2006.01)
*C01B 33/02* (2006.01)
*C01B 33/021* (2006.01)

(52) U.S. Cl.
CPC ........ *C01B 33/021* (2013.01); *C01P 2006/16* (2013.01); *Y10T 428/2982* (2015.01)

(56) References Cited

U.S. PATENT DOCUMENTS

| | | |
|---|---|---|
| 6,355,270 B1 | 3/2002 | Ferrari et al. |
| 2003/0059386 A1 | 3/2003 | Sumian et al. |
| 2003/0114633 A1 | 6/2003 | Martin et al. |
| 2004/0091421 A1* | 5/2004 | Aston .............. A61K 41/009 424/1.11 |
| 2005/0178287 A1 | 8/2005 | Anderson et al. |
| 2008/0280140 A1 | 11/2008 | Ferrari et al. |
| 2008/0311182 A1 | 12/2008 | Ferrari et al. |

FOREIGN PATENT DOCUMENTS

| | | |
|---|---|---|
| EP | 855179 | 7/1998 |
| EP | 1764152 | 3/2007 |
| WO | WO 2007/120248 | 10/2007 |
| WO | WO 2008/054874 | 5/2008 |

OTHER PUBLICATIONS

Alley et al., "Feasibility of Drug Screening with Panels of Human tumor Cell Lines Using a Microculture Tetrazolium Assay," Cancer Research, Feb. 1, 1988, 48:589-601.

Becker et al., "Peptide-polymer bioconjugates: hybrid block copolymers generated via living radical polymerizations from resin-supported peptides," Chem. Commun. (Camb), 2003:180-181.

Behrens et al., "Measuring a colloidal particle's interaction with a flat surface under nonequilibrium conditions," Eur. Phys. J. E, 2003, 10:115-121.

Bianco et al., "Monoclonal antibodies targeting the epidermal growth factor receptor," Curr Drug Targets, 2005, 6:275-287.

Bradbury, J., "Nanoshell destruction of inoperable tumours," Lancet Oneel, Dec. 2003, 4:711.

Buriak, J.M., "Organometallic chemistry on silicon and germanium surfaces," Chem. Rev . May 2002, 102(5): 1271-1308.

Canham, L. T., "Bioactive silicon structure fabrication through nanoetching techniques," Advanced Materials, 1995, 7(12):1033-1037.

Charnay et al., "Reduced Symmetry Metallodielectric Nanoparticles: Chemical Synthesis and Plasmonic Properties," J. Phys. Chem. B, 2003, 107:7327-7333.

Chen et al. "Soluble ultra-short single-walled carbon nanotubes," J. Am. Chem. Soc., 2006, 128:10568-10571.

Cheng et al. "Nanotechnologies for biomolecular detection and medical diagnostics," Curr. Opin. Chem. Biol., 2006, 10:11-19.

Chiapponi et al., "Tailored porous silicon microparticles: fabrication and properties", Chemphyschem., Apr. 6, 2010, v. 11, No. 5, pp. 1029-1035.

Ciardiello et al., "A novel approach in the treatment of cancer: targeting the epidermal growth factor receptor," Clin. Cancer Res., Oct. 2001, 7:2958-2670.

Cloninger M.J., "Biological applications of dendrimers," Curr. Opin. Chem. Biol., 2002, 6:742-748.

Cohen et al., "Microfabrication of Silicon-Based Nanoporous Particulates for Medical Applications," Biomedical Microdevices, 2003, 5(3):253-259.

Corot et al., "Recent advances in iron oxide nanocrystal technology for medical imaging," Adv. Drug Deliv. Rev., 2006, 58:1471-1504.

Conic et al., "Quantitative analysis and characterization of biofunctionalized fluorescent silica particles," Langmuir, 2006, 22:2731-2737.

Cullis et al,. "The structural and luminescence properties of porous silicon," J. Appl. Phys., Aug. 1, 1997, 82(3):909-965.

Cunin et al. "Biomolecular screening with encoded porous-silicon photonic crystals", Nature Materials, 2002, v. 1, pp. 39-41, www.nature.com/naturematerials.

Decuzzi et al., "A theoretical model tor the margination of particles within blood vessels," Ann. Biomed. Eng., Feb. 2005, 33(2):179-90.

Decuzzi et al., "Adhesion of microfabricated particles on vascular endothelium: a parametric analysis," Ann. Biomed. Eng., Jun. 2004, 32(6):793-802.

Decuzzi et al., "Fantastic voyages, Nanodevices in development today promise to give medicine capabilities that were once purely in the realm of fiction," Mechanical Engineering, Oct. 2006, 128:24-27.

Decuzzi et al., "The adhesive strength of non-spherical particles mediated by specific interactions," Biomaterials, 2006, 27:5307-5314.

Decuzzi et al., "The effective dispersion of nanovectors within the tumor microvasculature," Ann. Biomed. Eng., Apr. 4, 2006, 34(4):633-641.

Decuzzi et al., "The role of specific and non-specific interactions in receptor-mediated endocytosis of nanoparticles," Biomaterials, 2007, 28:2915-2922.

Derfus et al., "Probing the Cytotoxicity of Semiconductor Quantum Dots," Nano Lett., 2004, 4(1):11-18.

Desai et al., "Microfabricated immunoisolating biocapsules," Biotechnol. Bioeng., Jan. 5, 1998, 57(1):118-120.

Desai et al., "Nanoporous anti-fouling silicon membranes for biosensor applications," Biosens. Bioelectron., 2000, 15:453-462.

Druker, 8. J., "Perspectives on the development of a molecularly targeted agent," Cancer Cell, Feb. 2002, 1 :31-36.

Duncan R., "The dawning era of polymer therapeutics," Nat. Rev. Drug Discov., May 2003, 2:347-360.

Ferrari, M., "Cancer nanotechnology: opportunities and challenges," Na. Rev. Cancer, Mar. 2005, 5:161-171.

Ferrari, M., "Nanovector therapeutics," Curr. Opin. Chem. Biol., 2005, 9:343-346.

Foraker et al., "Microfabricated porous silicon particles enhance paracellular delivery of insulin across intestinal Caco-2 cell monolayers," Pharm. Res., Jan. 2003, 20(1):110-116.

Gardner P. "Microfabricated nanochannel implantable drug delivery devices: trends, limitations and possibilities," Expert Opin Drug Deliv, 2006, 3:479-487.

Gilles et al., "Designing Macromolecules for Therapeutic Applications : Polyester Dendrimer-Poly(ethylene oxide) 'Bow-Tie' Hybrids with Tunable Molecular Weight and Architecture," J. Am. Chem. Soc, 2002, 124:14137-14146.

Gonzalez-Mariscal et al., "Topical Review: Critical Role of Tight Junctions in Drug Delivery across Epithelial and Endothelial Cell Layers," J. Membrane Biol., 2005, 207:55-68.

He et al., "Bioconjugated Nanoparticles for DNA Protection from Cleavage," J. Am. Chem. Soc., 2003, 125:7168-7169.

Hirsch et al., "Nanoshell-mediated near-infrared thermal therapy of tumors under magnetic resonance guidance," Proc. Natl. Acad. Sci. USA, Nov. 11, 2003, 100(23): 13549-13554.

Hobday et al., "Molecularly targeted therapies for breast cancer," Cancer Control, 2005, 12(2):73-81.

International Search Report and Written Opinion dated Jun. 13, 2008, in corresponding PCT/US2007/075516, 9 pages.

Ishii et al., "Chaperonin-mediated stabilization and ATP-triggered release of semiconductor nanoparticles," Nature, Jun. 5, 2003, 423:628-632.

Kerbel et al., "Antiangiogenic Therapy: A Universal Chemosensitization Strategy for Cancer?" Science, May 26, 2006, 312:1171-1175.

(56) References Cited

OTHER PUBLICATIONS

Kim et al. "Near-infrared fluorescent type II quantum dots for sentinel lymph node mapping," Nat. Biotechnol., Jan. 2004, 22(1):93-97.
Lan et al., "Surface modification of silicon and gold-patterned silicon surfaces for improved biocompatibility and cell patterning selectivity," Biosens. Bioelectron. 2005, 20:1697-708.
Landen et al., "Therapeutic EphA2 Gene Targeting in vivo Using Neutral Liposomal Small Interfering RNA Delivery," Cancer Res., Aug. 1, 2005, 65(15):6910-6918.
Langer, Robert, "Drug delivery and targeting," Nature, Apr. 30, 1998, 392(Supp):5-10.
Lasic, D. D., "Doxorubicin in sterically stabilized liposomes," Nature, Apr. 11, 1996, 380:561-562.
LaVan et al., "Small-scale systems for in vivo drug delivery," Nat. Biotechnol., Oct. 2003, 21 (10):1184-1191.
Li et al. "Porous-Silicon/Polymer Nanocomposite Photonic Crystals Formed by Microdroplet Patterning", Adv. Mater. 2005, v. 17, pp. 1249-1251.
Li et al., "Doxorubicin physical state in solution and inside liposomes loaded via a pH gradient," Biochimica et Biophysica Acta, 1998, 1415:23-40.
Lin et al., "A porous silicon-based optical interferometric biosensor," Science, Oct. 31, 1997, 278:840-843.
Liu et al., "In vivo biodistribution and highly efficient tumour targeting of carbon nanotubes in mice," Nature Nanotechnology, Jan. 2007, 2:47-52.
Loo et al., "Nanoshell-Enabled Photonics-Based Imaging and Therapy of Cancer," Technol. Cancer Res. Treat., Feb. 2004, 3(1):33-40.
Low et al., "Evaluation of mammalian cell adhesion on surface-modified porous silicon." Biomaterials, 2006, 27(26): 4538-4546.
Mansur et al., "Biomaterial with chemically engineered surface for protein immobilization," J. Mater. Sci. Mater. Med., 2005, 16:333-340.
Mayne et al., "Biologically Interfaced Porous Silicon Devices." Physica Status Solidi, 2000, 182(1):505-513.
Meade et al., "Microfabrication of freestanding porous silicon particles containing spectral barcodes," phys. stat. sol. (RRL), 2007, 1(2):R71-R-73.
Meade et al., "Porous Silicon Photonic Crystals as Encoded Microcarriers," Advanced Materials, Oct. 18, 2004, 16(20), 1811-1814.
Moghimi et al., "Nanomedicine: current status and future prospects," Faseb J., Mar. 2005, 19:311-330.
Nakanishi et al., "Development of the polymer micelle carrier system for doxorubicin," J. Control. Release, 2001, 74:295-302.
O'Neal et al., "Photo-thermal tumor ablation in mice using near infrared-absorbing nanoparticles," Cancer Lett., 2004, 209:171-176.
Oyewumi et al., "Engineering Tumor-Targeted Gadolinium Hexanedione Nanoparticles for Potential Application in Neutron Capture Therapy," Bioconjug. Chem., 2002, 13:1328-1335.
Paik et al., "Micromachining of mesoporous oxide films for microelectromechanical system structures," J. Mater. Res., Aug. 2002, 17(8):2121-2129.
Prestidge et al., "Mesoporous silicon: a platform for the delivery of therapeutics," Expert Opin. Drug Deliv., 2007, 4(1):101-110.
Quintana et al., "Design and Function of a Dendrimer-Based Therapeutic Nanodevice Targeted to Tumor Cells Through the Folate Receptor," Pharm. Res., Sep. 2002, 19(9):1310-1316.
Raja et al., "Hybrid Virus-Polymer Matreials. 1. Synthesis and Properties of PEG-Decoraged Cowpea Mosaic Virus," Biomacromolecules, 2003, 4:472-476.
Saini et al., "Covalent sidewall functionalization of single wall carbon nanotubes," J. Am. Chem. Soc., 2003, 125:3617-3621.
Sakamoto et al., "Anti-Biological Barrier Nanovector Technology for Cancer Applications," Expert Opin. Drug Deliv., 2007, 4(4):359-369.
Salonen et al., "Mesoporous Silicon in Drug Delivery Applications," Journal of Pharmaceutical Sciences, Feb. 2008, 97(2):632-653.
Salonen et al., "Mesoporous silicon microparticles for oral drug delivery: Loading and release of five model drugs," Journal of Controlled Release, 2005, 108:362-374.
Schreiber, F., "Structure and growth of self-assembling monolayers," Progress in Surface Science, 2000, 65:151-256.
Shriver-Lake et al., "Antibody immobilization using heterobifunctional crosslinkers." Biosens. Bioelectron., 1997, 12(11):1101-1106.
So et al., "Self-illuminating quantum dot conjugates for in vivo imaging," Nat. Biotechnol., Mar. 2006, 24(3):339-343.
Soppimath et al., "Biodegradable polymeric nanoparticles as drug delivery devices," J. Control. Release, 2001, 70: 1-20.
Starodub et al., "Antibody immobilisation on the metal and silicon surfaces. The use of self-assembled layers and specific receptors," Bioelectrochemistry, 2005, 66: 111-115.
Sullivan et al., "Nanotechnology and tumor imaging: seizing an opportunity," Mol. Imaging, Oct. 2004, 3(4):364-369.
Tasciotti et al., "Mesoporous silicon particles as a multistage delivery system for imaging and therapeutic applications," Nature Nanotechnology, Mar. 2008, 3:151-158.
Thomas et al. "Delivery of nanogram payloads using magnetic porous silicon microcarriers," Lab Chip, 2006, 6:782-787.
Torchilin, V. P., "Multifunctional nanocarriers," Adv. Drug Deliv. Rev., 2006, 58:1532-1555.
Uziely et al., "Liposomal doxorubicin: antitumor activity and unique toxicities during two complementary phase I studies," J. Clin. Oncol., 1995, 13(7):1777-1785.
Vijayanathan et al., "DNA Nanoparticles and Development of DNA Delivery Vehicles for Gene Therapy," Biochemistry, Dec. 3, 2002, 41(48):14085-14094.
Wang et al., "Nanotechnology for targeted cancer therapy," Expert Rev. Anticancer Ther., 2007, 7(6):833-837.
Wang et al., "Surface modification of micromachined silicon filters," Journal of Materials Science, 2000, 35:4923-4930.
Yan et al., "Synthesis and Characterization of Silica-Embedded Iron Oxide Nanoparticles for Magnetic Resonance Imaging," J. Nanosci. Nanotechnol., 2004, 4(1/2):72-76.
Yan et al., "The Embedding of Meta-tetra(Hydroxyphenyl)-Chlorin into Silica Nanparticle Platforms for Photodynamic therapy and Their Singlet Oxygen Production and pH-dependent Optical Properties," Photoch. Photobiol., 2003, 78(6):587-591.
Yokokawa et al., "Mechanical properties of aerogel-like thin films used for MEMS," J. Micromech. Microeng., 2004, 14:681-686.
Zhang et al., "Proteins and cells on PEG immobilized silicon surfaces," Biomaterials, 1998, 19:953-60.
Meade, S.O. and Sailor, M.J., "Microfabrication of freestanding porous silicon particles containing spectral barcodes", Phys. Stat. Sol. (RRL) 1, No. 2, R71-R73 (2007).

* cited by examiner

FIGURES 9B-C
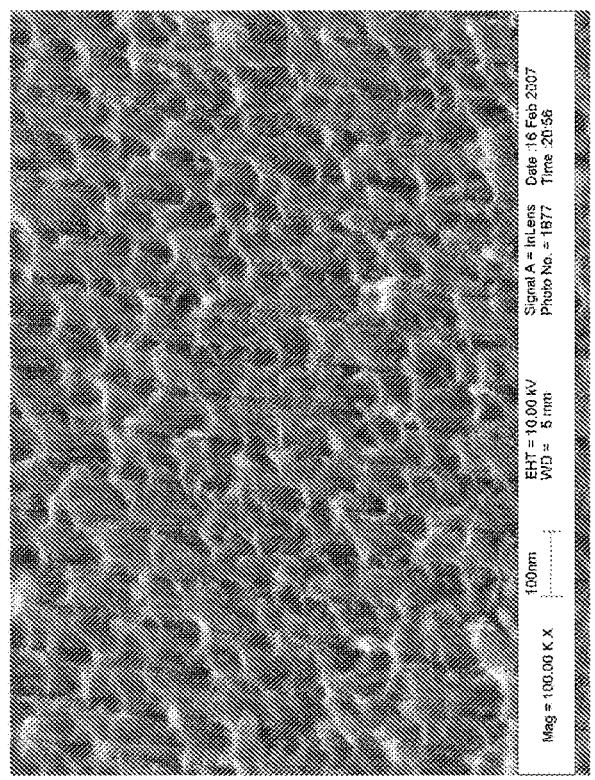
C
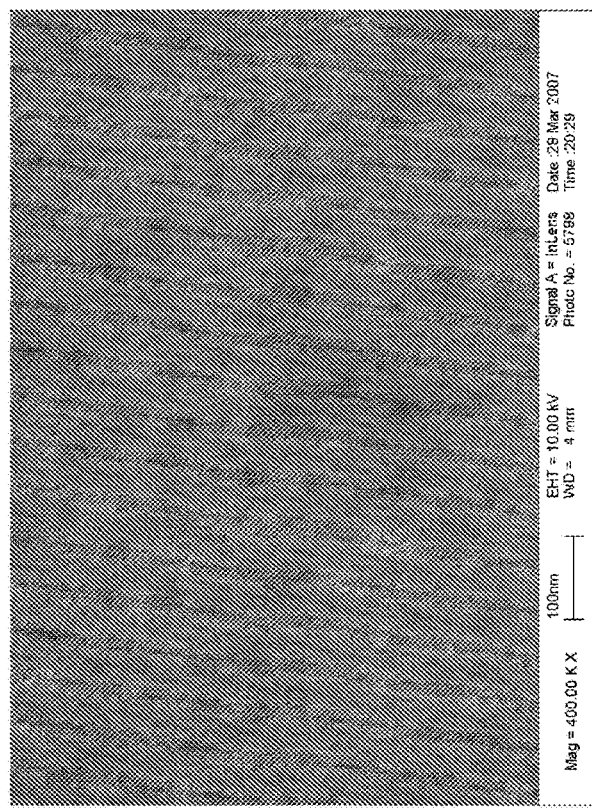
B

POROUS PARTICLES AND METHODS OF
MAKING THEREOF

CROSS-REFERENCE TO RELATED
APPLICATIONS

This application is a continuation of U.S. patent application Ser. No. 12/110,5151,filed on Apr. 28, 2008 which claims the benefit under 35 U.S.C. § 119(e) of U.S. Provisional Patent Application No. 60/914,358 filed Apr. 27, 2007 and U.S. Provisional Patent Application No. 60/914,348 filed Apr. 27, 2007, and is a continuation-in-part under 35 U.S.C. § 120 of U.S. patent application Ser. No. 11/836,004 filed Aug. 8, 2007, the disclosures of each of which are hereby incorporated herein by reference.

STATEMENT REGARDING FEDERALLY
SPONSORED RESEARCH OR DEVELOPMENT

This invention was made with government support under Grant No. W81XWH-04-2-0035, awarded by the U.S. Department of Defense and Grant No. SA23-06-017 awarded by NASA. The government has certain rights in this invention.

BACKGROUND

Technical Field

The present application relates generally to the field of nanotechnology and, in particular, to porous particles and methods of making thereof.

Description of Related Art

Porous particles, such as porous silicon particles and porous silica particles, have a number of applications including being used as drug delivery carriers. For example, porous silicon particles and methods of their making are disclosed in the following documents: U.S. Pat. Nos. 6,355,270 and 6,107,102; US patent publication no. 2006/0251562; Cohen et al., Biomedical Microdevices 5:3, 253-259, 2003; Meade et al., Advanced Materials, 2004, 16(20), 1811-1814; Thomas et al. Lab Chip, 2006, 6, 782-787; Meade et al., phys. stat. sol. (RRL) 1(2), R71-R-73 (2007); Salonen et al. Journal of Pharmaceutical Sciences 97(2), 2008, 632-653; Salonen et al. Journal of Controlled Release 2005, 108, 362-374.

A need exists for new types of porous particles and new methods of making them.

SUMMARY

One embodiment is a particle comprising a body defined by an outer surface, wherein the body comprises a first porous region and a second porous region, that differs from the first region in at least one property selected from the group consisting of a pore density, a pore size, a pore shape, a pore charge, a pore surface chemistry, and a pore orientation.

Another embodiment is a composition comprising a plurality of particles, wherein each particle of the plurality comprises a body defined by an outer surface, wherein the body comprises a first porous region and a second porous region, that differs from the first region in at least one property selected from the group consisting of a pore density, a pore size, a pore shape, a pore charge, a pore surface chemistry, and a pore orientation.

Yet another embodiment is a particle comprising a body defined by an outer surface, wherein the body comprises a wet etched porous region and wherein the particle does not include a nucleation layer associated with wet etching.

Yet another embodiment is a composition comprising a plurality of particles that each have a body defined by an outer surface, wherein the body comprises a wet etched porous region and wherein the particle does not include a nucleation layer associated with wet etching.

And yet another embodiment is a method of making porous particles comprising providing a substrate having a surface; forming a first porous layer in the substrate; patterning one or more particles on the substrate; forming in the substrate a second porous layer having a porosity larger that that of the first porous; and releasing the patterned one or more particles from the substrate, wherein the releasing comprises breaking the second porous layer and wherein the released one or more particles contain at least a portion of the first porous layer. And yet another embodiment is a method of making porous particles comprising providing a substrate having a surface; forming a first porous layer in the substrate via wet etching; removing a nucleation layer associated with the wet etching; patterning one or more particles on the surface of the substrate; and releasing the patterned one or more particles from the substrate, wherein the released one or more particles contain at least a portion of the first porous layer.

DRAWINGS

FIG. 1(A)-(B) schematically illustrate a method of fabricating porous particles that involves releasing particles from a substrate via electropolishing.

FIG. 2(A)-(B) schematically illustrate a method of fabricating porous particles that involves releasing particles from a substrate via formation of a release porous layer.

FIG. 3 schematically illustrates of a method of fabricating porous particles, in which a formation of a porous layer on a substrate precedes patterning of particles.

FIG. 4 schematically illustrates a method of fabricating porous particles, in which formation of multiple porous layers on a substrate precedes patterning of particles.

FIG. 5 schematically illustrates a method of fabricating porous particles, in which patterning of particles on a substrate precedes formation of multiple porous layers.

Figure 9A:
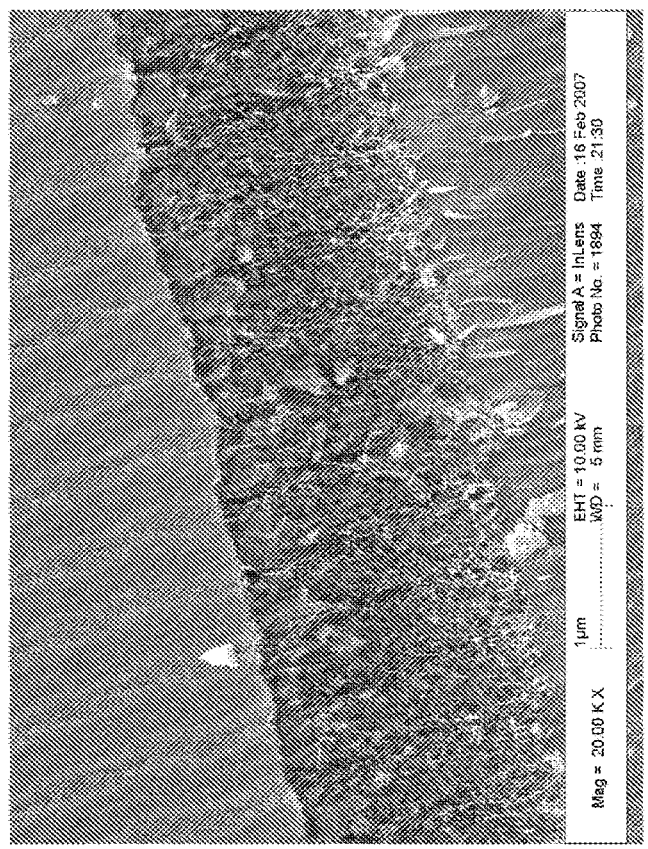

FIG. 9A-C present SEM images of a porous silicon film with a nucleation layer (FIGS. 9A-B) and a porous silicon film without a nucleation layer (FIG. 9C).

Figure 10:
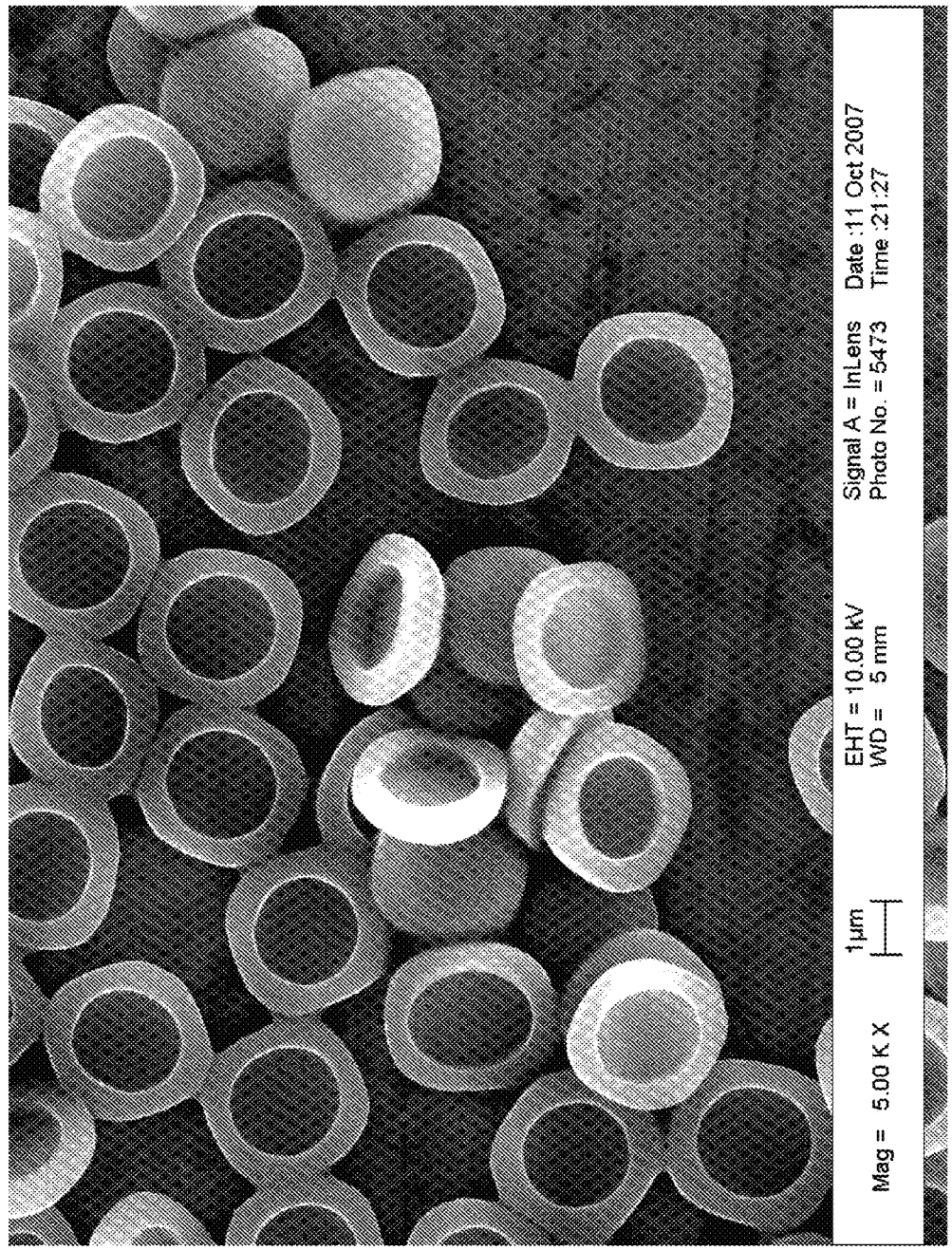

FIG. 10 presents an SEM image of 3.2 micron silicon particles with a 500 nm trench formed by silicon RIE etching.

Figure 11:
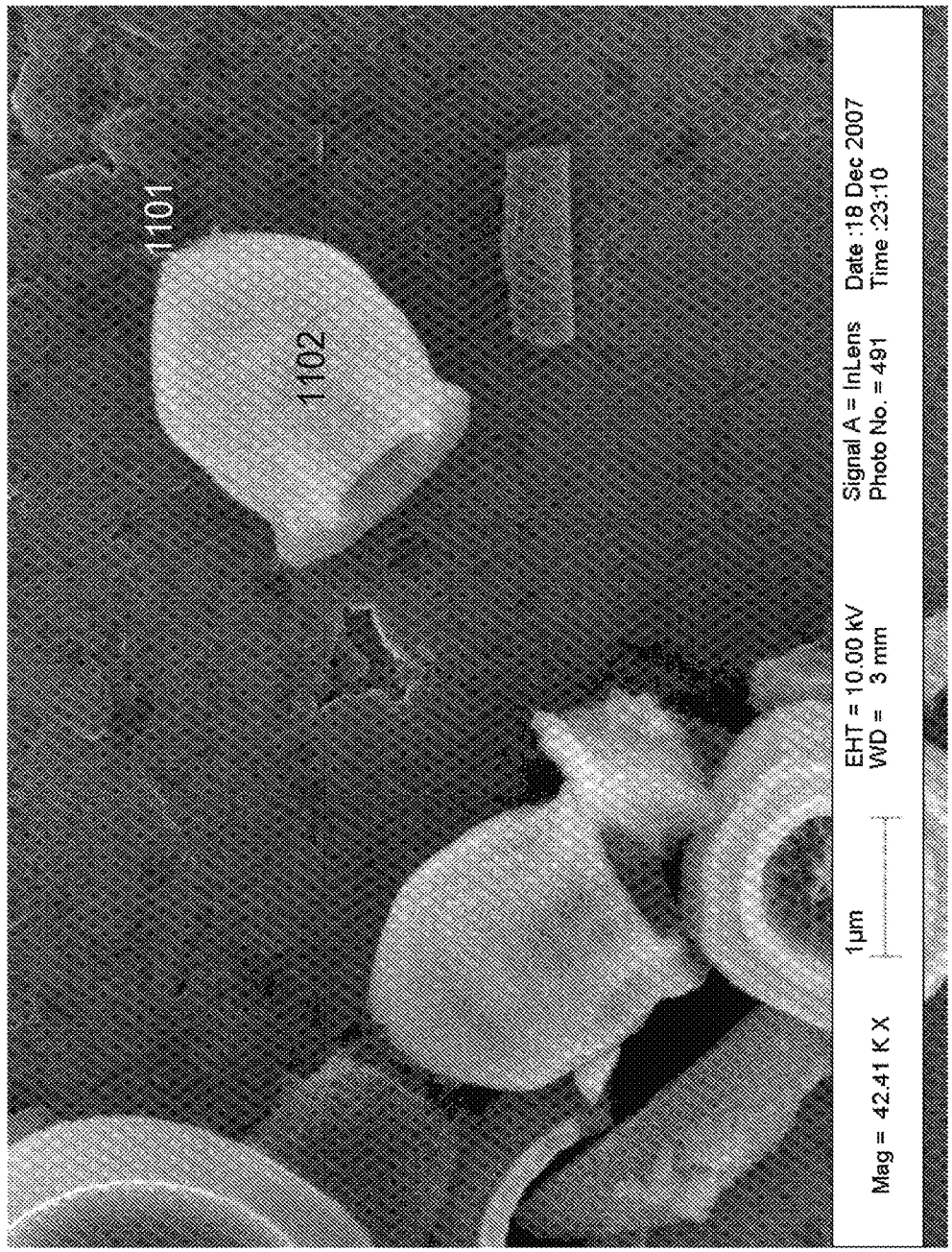

FIG. 11 presents an SEM image of silicon particles with a 1.5 μm trench formed by silicon etching.

Figure 12:
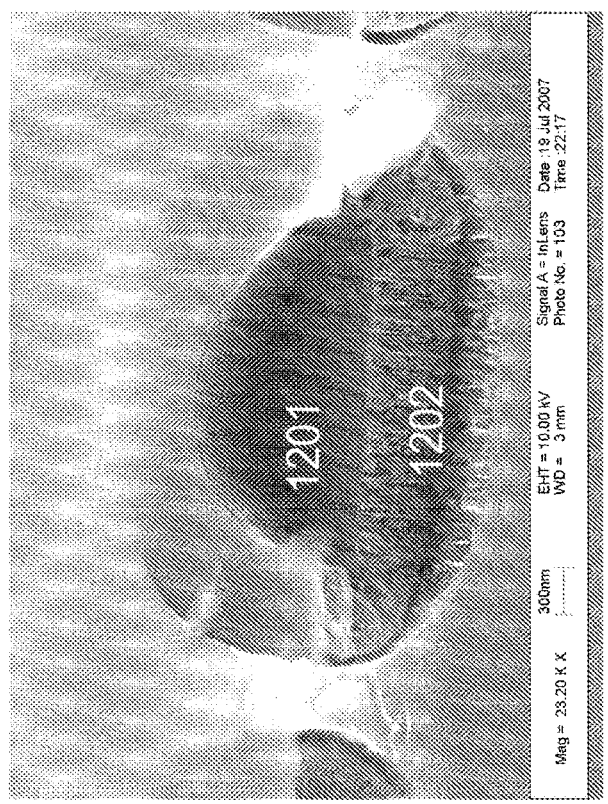
Figure 12:
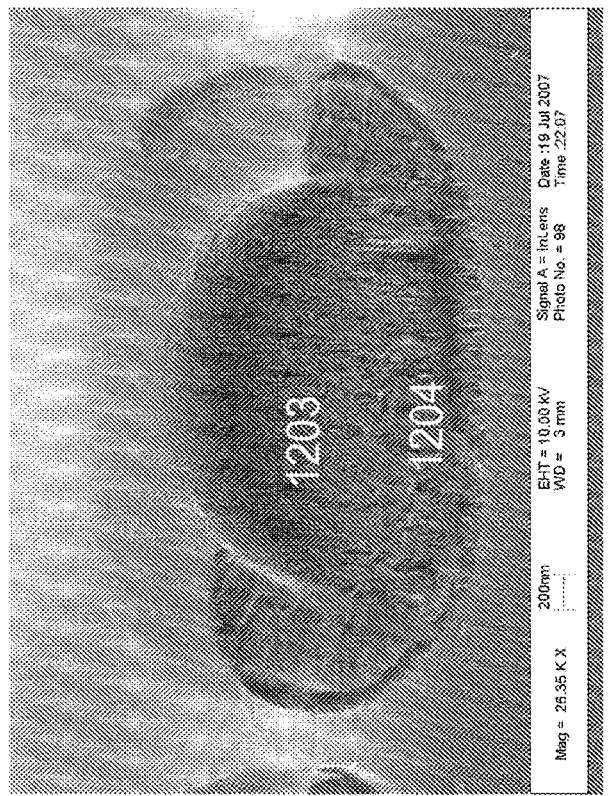

FIG. 12 presents two SEM images of silicon particles: the left image shows a particle with a nucleation layer, while the right image shows a particle, on which a nucleation layer has been removed by RIE.

Figure 13:
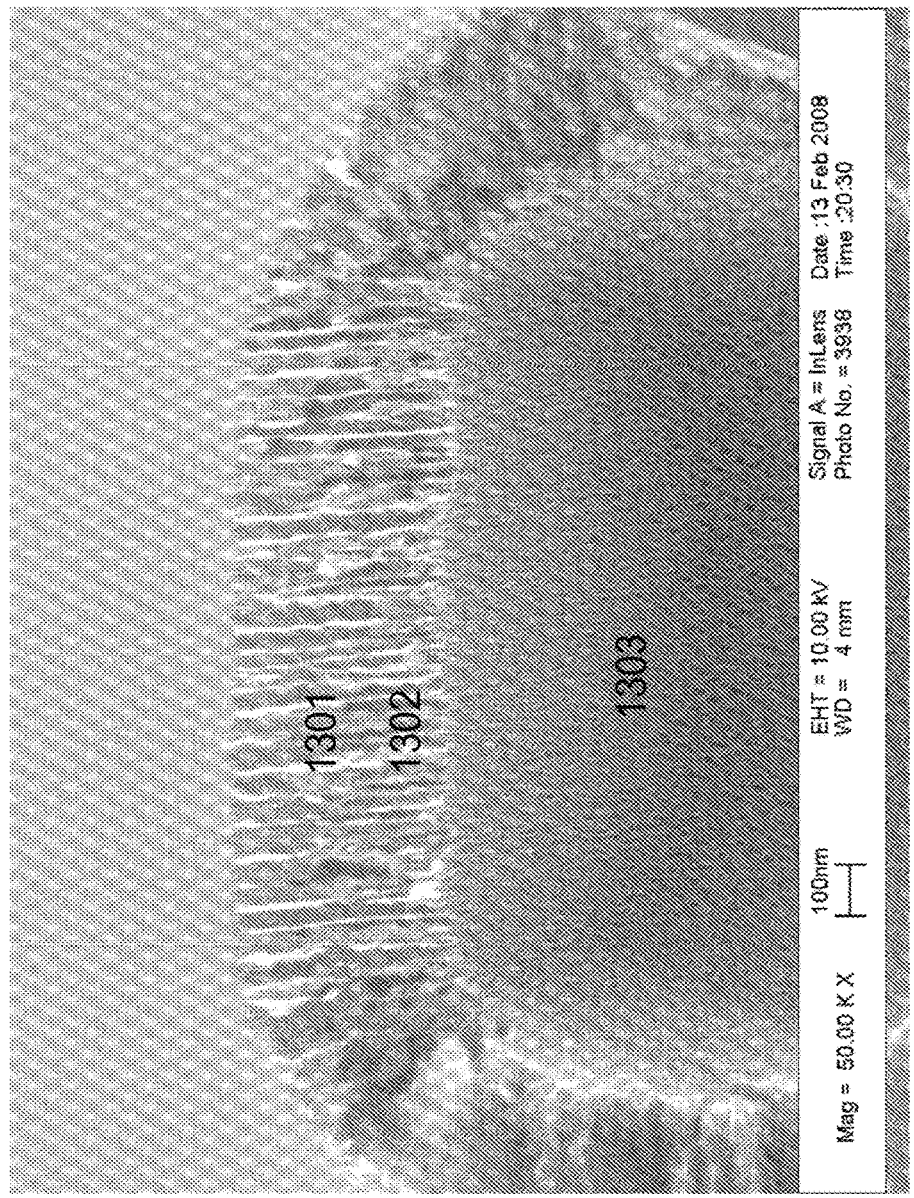

FIG. 13 is an SEM cross-section image of a silicon particle with two different porous regions along a longitudinal direction.

DETAILED DESCRIPTION

The following documents, which are all incorporated herein by reference in their entirety, may be useful for understanding of the present inventions:
1) PCT publication no. WO 2007/120248 published Oct. 25, 2007;
2) US Patent Application Publication no. 2003/0114366;
3) U.S. patent application Ser. No. 11/641,970 filed Dec. 20, 2006;
4) U.S. patent application Ser. No. 11/870,777 filed Oct. 10, 2007;
5) U.S. patent application Ser. No. 12/034,259 filed Feb. 20, 2008;
6) Tasciotti et al., Nature Nanotechnology, vol. 3, 151-158, 2008.

Definitions

Unless otherwise specified "a" or "an" means one or more.

"Nanoporous" or "nanopores" refers to pores with an average size of less than 1 micron.

"Biodegradable" refers to a material that can dissolve or degrade in a physiological medium or a biocompatible polymeric material that can be degraded under physiological conditions by physiological enzymes and/or chemical conditions.

"Biocompatible" refers to a material that, when exposed to living cells, will support an appropriate cellular activity of the cells without causing an undesirable effect in the cells such as a change in a living cycle of the cells; a change in a proliferation rate of the cells and a cytotoxic effect.

"Microparticle" refers to a particle having a maximum dimension from 1 micrometer to 1000 micrometers, or, in some embodiments from 1 micron to 100 microns as specified. "Nanoparticle" refers to a particle having a maximum dimension of less than 1 micron.

The present inventors developed new porous particles and new methods of making porous particles. According to the first embodiment, a particle may comprise a body defined by an outer surface, such that the body includes a first porous region and a second porous region, that differs from the first region in at least one property, such as a pore density, a pore size, a pore shape, a pore charge, a pore surface modification or a pore orientation.

The particle having two different porous regions may be used, for example, for loading two different populations of smaller particles, which may comprise at least one active agent such as a therapeutic agent or an imaging agent, as disclosed in a co-pending U.S. application Ser. No. 11/836, 004.

In some embodiments, at least one of the first and a second porous region may be composed of a porous oxide material or a porous etched material. In certain embodiments, both the first and second porous regions may be composed of a porous oxide material or a porous etched material. Examples of porous oxide materials include, but not limited, porous silicon oxide, porous aluminum oxide, porous titanium oxide and porous iron oxide. The term "porous etched materials" refers to a material, in which pores are introduced via a wet etching technique, such as electrochemical etching. Examples of porous etched materials include porous semiconductors materials, such as porous silicon, porous germanium, porous GaAs, porous InP, porous SiC, porous $Si_xGe_{1-x}$, porous GaP, porous GaN.

In many embodiments, the first and the second porous regions comprise porous silicon. In many embodiments, at least a portion of or the whole body of the particles is composed of porous silicon.

The body of the particle may have a regular, i.e. non-random shape, in at least one cross section or as viewed from at least one direction using, for example, a microscopic technique, such as SEM. Non-limiting examples of such regular shapes include a semispherical, a bowl, a frustum, a pyramid, a disc.

The dimensions of the particle are not particularly limited and depend on an application for the particle. For example, for intravascular administration, a maximum characteristic size of the particle can be smaller than a radius of the smallest capillary, which is about 4 to 5 microns in humans.

In some embodiments, the maximum characteristic size of the particle may be less than about 100 microns or less than about 50 microns or less than about 20 microns or less than about 10 microns or less than about 5 microns or less than about 4 microns or less than about 3 microns or less than about 2 microns or less than about 1 micron. Yet in some embodiments, the maximum characteristic size of the particle may be from 500 nm to 3 microns or from 700 nm to 2 microns. Yet in some embodiments, the maximum characteristic size of the particle may be greater than about 2 microns or greater than about 5 microns or greater than about 10 microns.

In some embodiments, the first porous region may differ from the second porous region in a pore size, i.e. a pore size of pores in the first porous region may be larger than a pore size in the second region or vice versa. For example, a pore size in one of the first and the second porous region may be at least 2 times, or at least 5 times, or at least 10 times, or at least 20 times or at least 50 times, or from 2 to 50 times or from 5 to 50 times or from 2 to 20 times or from 5 to 20 times larger than a pore size in the other of the first and the second porous region.

In many embodiments, at least one of the first and the second porous regions can be a nanoporous region. In certain embodiments, both the first and the second porous regions can be nanoporous regions.

In some embodiments, a pore size in at least one of the first and the second porous regions may be from about 1 nm to about 1 micron or from about 1 nm to about 800 nm or from about 1 nm to about 500 nm or from about 1 nm to about 300 nm or from about 1 nm to about 200 nm or from about 2 nm to about 100 nm.

In some embodiments, at least one of the first and the second porous regions can have an average pore size of no more than 1 micron or no more than 800 nm or more than 500 nm or more than 300 nm or no more than 200 nm or no more than 100 nm or no more than 80 nm or no more than 50 nm. In certain embodiments, both the first and the second porous regions can have their respective average pore size of no more than 1 micron or no more than 800 nm or more than 500 nm or more than 300 nm or no more than 200 nm or no more than 100 nm or no more than 80 nm or no more than 50 nm. In some embodiments, at least one of the first and the second porous regions can have an average pore size from about 10 to about 60 nm or from about 20 to about 40 nm.

In some embodiments, at least one of the first and the second porous regions can have an average pore size from about 1 nm to about 10 nm or from about 3 nm to about 10 nm or from about 3 nm to about 7 nm.

In some embodiments, one of the first and the second porous regions can have an average pore size from about 10 to about 60 nm or from about 20 to about 40 nm, while the other of the first and the second porous regions can have an average pore size from about 1 nm to about 10 nm or from about 3 nm to about 10 nm or from about 3 nm to about 7 nm.

In some embodiments, pores of the first porous region and the second porous regions may have the same or substantially the same orientation but have different average sizes.

In general, pores sizes may be determined using a number of techniques including $N_2$ adsorption/desorption and microscopy, such as scanning electron microscopy.

In some embodiments, the first porous region and the second porous region may have different pore orientations. For instance, the outer surface of the particle may include a planar subsurface and pores of the first porous region may be perpendicular or substantially to the subsurface, while pores of the second porous region may be oriented in a direction, that is substantially different from the perpendicular direction, such as a direction parallel to the subsurface. Pore orientation may be determined using a microscopic technique such as SEM.

In some embodiments, pores of at least one of the first and second porous regions may be linear pores. In some embodiments, pores of both the first and second porous regions may be linear pores.

In some embodiments, pores of at least one of the first and second porous regions may be sponge like pores. In some embodiments, pores of both the first and second porous regions may be sponge like pores.

In some embodiments, pores of one of the first and second porous regions may be linear pores, while pores of the other of the first and second porous regions may be sponge like pores.

In some embodiments, pores of the first and second porous regions may have different pore surface charges. For example, a pore surface of the first porous region may be positively charged, while a pore surface of the second porous region may neutral or negatively charged.

In some embodiments, pores of the first and second porous regions may have different shapes. For example, pores of one of the first and second porous regions may cylindrical pores, while pores of the other of the first and second porous regions may be non-cylindrical pores. Pores shape may be determined using a microscopic technique, such as SEM.

In some embodiments, pores of the first and second porous regions may have different surface chemistry. A pore surface of the first porous region may be chemically modified with a first surface group, while a pore surface of the second porous region may be unmodified or chemically modified with a second surface group, which is different from the first surface group. For example, the pore surface of the first porous region may be silanized with an aminosilane, such as 3-aminopropyltriethoxysilane, while the pore surface of the second porous region may be silanized with a mercaptosilane, such as 3-mercaptopropyltrimethoxysilane.

In some embodiments, pores of the first and second porous regions may have different porous density. For example, the first porous region may have a higher porous density and vice versa.

In some embodiments, at least one of the first and second porous regions may be a biodegradable region. In some embodiments, both of the first and second porous regions may be biodegradable. In some embodiments, the whole body of the particle may be biodegradable.

In general, porous silicon may be bioinert, bioactive or biodegradable depending on its porosity and pore size. Also, a rate or speed of biodegradation of porous silicon may depend on its porosity and pore size, see e.g. Canham, Biomedical Applications of Silicon, in Canham LT, editor. Properties of porous silicon. EMIS datareview series No. 18. London: INSPEC. p. 371-376. The biodegradation rate may also depend on surface modification. Thus, the particle may be such that the first porous region has a first rate of biodegradation, while the second porous region has a second rate of biodegradation, which is different from the first biodegradation rate.

In some embodiments, each the first porous and second regions may have a thickness, or the smallest characteristic dimension of more than 200 nm or more than 250 nm or more than 300 nm.

In some embodiments, the particle may be free or substantially free of a nucleation layer, which is an irregular porous layer, which is usually formed at the initial stage of electrochemical wet etching, when the etching solution starts to penetrate into a substrate. A thickness of the nucleation layer may depend on parameters of an etched substrate and electrochemical etching process. For the substrate's and etching parameters, that can be used to produce nanosized pores, a thickness of the nucleation layer can be from 1 nm to about 200 nm.

In some embodiments, the outer surface of the particle may have a surface chemistry different from a surface chemistry of at least one of the first and the second porous regions. Yet, in some embodiment, the outer surface of the particle may have a surface chemistry different from a surface chemistry of both the first and the second porous regions.

The particle may be a top-down fabricated particle, i.e. a particle produced utilizing top-down microfabrication or nanofabrication technique, such as photolithography, electron beam lithography, X-ray lithography, deep UV lithography, nanoimprint lithography or dip pen nanolithography. Such fabrication methods may allow for a scaled up production of particles that are uniform or substantially identical in dimensions.

Thus, the present inventions also provide a composition comprising a plurality of particles, wherein each particle of the plurality comprises a body defined by an outer surface, wherein the body comprises a first porous region and a second porous region, that differs from the first region in at least one property selected from the group consisting of a pore density, a pore size, a pore shape, a pore charge, a pore surface chemistry, and a pore orientation.

According to a second embodiment, a particle may comprise a body defined by an outer surface, wherein the body comprises a wet etched porous region, i.e. a porous region produced by a wet etching technique, such as an electrochemical wet etching, and wherein the particle does not include a nucleation layer associated with wet etching.

The particle of the second embodiment may have the same dimensions and shape as discussed above for the particle of the first embodiment. The wet etched porous region may have the same properties as properties of the first or the second porous regions of the particle of the first embodiment. The outer surface of the particle of the second embodiment may have the same properties as the outer surface of the particle of the second embodiment. As the particle of the first embodiment, the particle of the second embodiment may be a top-down fabricated particle.

The particle of the second embodiment may be a part of a composition that includes a plurality of particles, that are uniform in dimension and are substantially identical to the particle. The particles of the first and second embodiments may prepared according to methods of making porous particles that are detailed below. Particles of the present inventions may be used for a variety of applications including drug delivery. In certain cases, an active agent, such as a therapeutic agent or an imaging agent, may be loaded directly in pores of the particles. Yet in some cases, smaller size particles, which in turn comprise an active agent may be loaded in the pores as disclosed, for example, in U.S. application Ser. No. 11/836,004.

Methods of Making Porous Particles

A method of making porous particles may involve providing a substrate, forming a porous layer on a surface of the substrate, patterning one or more particles on a substrate and releasing the particles from the substrate, so that an individual released particle includes a portion of the porous layer. The porous layer formation and the patterning may be performed in a direct or reverse order. In other words, in some cases, the porous layer formation may precede the patterning, while, in some other embodiments, the porous layer formation may follow the patterning. The methods of the present inventions utilize micro/nanofabrication techniques, which have the following advantages 1) capability to make particles having a variety of predetermined shapes including but not limited to spherical, square, rectangular and ellipse; 2) very precise dimensional control; 3) control over porosity and pore profile; 4) complex surface modification is possible.

Substrate

The substrate may be composed of any of a number of materials. Preferably, the substrate has at least one planar surface, on which one or more particles can be patterned. Preferably, the substrate comprises a wet etchable material, i.e. the material that can be porosified by a wet etching technique, such as electrochemical etching.

In certain embodiments, the substrate may be a crystalline substrate, such a wafer. In certain embodiments, the substrate may be a semiconducting substrate, i.e. a substrate comprising one or more semiconducting materials. Non-limiting examples of semiconducting materials include Ge, GaAs, InP, SiC, $Si_xGe_{1-x}$, GaP, and GaN. In many embodiments, it may be preferred to utilize silicon as the substrate's material. Properties of the substrate, such as doping level, resistivity and a crystalline orientation of the surface, may be selected to obtain desired properties of pores.

Forming Porous Layer

The porous layer may be formed on the substrate using a number of techniques. Preferably, the porous layer is formed using a wet etching technique, i.e. by exposing the substrate to an etching solution that includes at least one etchant, such as a strong acid. Particular etchant may depend on the material of the substrate. For example, for germanium substrates, such an etchant may be a hydrochloric acid (HCl), while for silicon substrates the etchant may be a hydrofluoric etchant. Preferably, the formation of the porous layer is performed using an electrochemical etching process, during which an etching electric current is run through the substrate. Electrochemical etching of silicon substrates to form porous silicon layers is detailed, for example, in Salonen et al., Journal of Pharmaceutical Sciences, 2008, 97(2), 632. For electrochemical etching of silicon substrates, the etching solution may include, in addition to HF, water and/or ethanol.

In some embodiments, during the electrochemical etching process, the substrate may act as one of the electrodes. For example, during the electrochemical etching of silicon, the silicon substrate may act as an anode, while a cathode may be an inert metal, such as Pt. In such a case, a porous layer is formed on a side of the substrate facing away from the inert metal cathode. Yet in some other embodiments, during the electrochemical etching, the substrate may be placed between two electrodes, which each may comprise an inert metal.

The electrochemical etching process may be performed in a reactor or a cell resistant to the etchant. For example, when the etchant is HF, the electrochemical etching process may be performed in a reactor or a cell comprising an HF-resistant material. Examples of HF-resistant materials include fluoropolymers, such as polytetrapfruoroethylene. The electrochemical etching may be performed by monitoring a current at one of the electrodes, e.g. by monitoring anodic current, (galvanostatically) or voltage (potentiostatically). In some embodiments, it may be preferable to perform electrochemical etching at a constant current density, which may allow for a better control of the formed porous layer properties and/or for a better reproducibility from sample to sample.

In some embodiments, if the formation of two different stable porous regions is desired, two different constant currents may be applied. For example, a first current density may applied to form a first stable porous layer and then a second current density may be applied to form a second stable porous layer, which may differ from the first stable porous layer in a pore size and/or porosity.

In some embodiments, parameters of the formed porous layer, such as pore size, porosity, thickness, pore profile and/or pore shape, and thus the respective parameters of the fabricated particles may be tuned by selecting parameters of the electrochemical etching process, such as a concentration and a composition of the etching solution, applied electrical current (and potential), etching time, temperature, stirring conditions, presence and absence of illumination (and parameters of illumination, such as intensity and wavelength) as well as parameters the etched substrate, such as the substrate's composition, the substrate's resistivity, the substrate's crystallographic orientation and the substrate's level and type of doping.

In some embodiments, along the pores in the formed porous layer may have a predetermined longitudinal profile, which is a profile perpendicular or substantially perpendicular to the surface of the substrate. Such longitudinal profile may be generated by varying the electrical current density during the electrochemical etching. For longitudinal pores in the porous layer, both porosity and pore size may be varied. Accordingly, in some embodiments, a profiled pore in the porous layer and in the fabricated porous particles may have a smaller size at top, i.e. at the surface of the substrate, and a larger pore at bottom, i.e. deeper in the substrate. Yet in some embodiments, a profiled pore in the porous layer and in the fabricated porous particles may have a larger size at the top, and a small size at the bottom. In some embodiments, profiled pores in the porous layer and in the fabricated particles may also have different porosity at the top and at the bottom.

In many embodiments, the electrochemical etching may start with a pulse of a larger electrical current for a short time to prevent or reduce the formation of a nucleation layer. The nucleation layer may be also removed by etching the nucleation layer after the formation of the porous layer. Such etching may be performed by dry etching technique, such as RIE. An appropriate measure may be taken to protect the areas underneath. For example, a photoresist may be placed on the surface, and planation may be performed by baking, and then plasma etch-back may be applied to expose a portion of the surface of the substrate that has to be etched.

For electrochemical etching, a backside of the substrate, i.e. the side of the substrate opposite to the one of which the porous layer is formed, may be coated with a conductive layer, such as a metal layer, to ensure electrical contact. Such a conductive layer may be coated using a number of techniques, including thermal evaporation and sputtering.

Nucleation Layer

During the electrochemical etching, the etching solution can start its pore formation through a formation of a nucleation layer, which is a surface layer of the substrate and in which pores have properties different from the desired properties of the porous layer. The nucleation layer may be characterized by irregularities of its pore properties and associated surfaces roughness, which may on a scale larger than a pore size.

In many applications, the nucleation layer on the surface of porous particles is undesirable. For example, when the silicon porous particles are used for loading smaller size particles inside them, the nucleation layer on the surface of the larger may reduce loading efficiency.

In some embodiments, a nucleation layer is removed or prevented from forming. In some embodiments, during the electrochemical etching, prior to applying a current to produce the desired pores in the porous layer, a larger current may be applied to prevent the formation of the nucleation layer. Yet in some embodiments, after the formation of the porous layer, the nucleation layer may be removed by dry etching, such as RIE.

Patterning

Patterning the one or more particles on a surface of the substrate may be performed using any of a number of techniques. In many embodiments, the patterning may be performed using a lithographic technique, such as photolithography, X-ray lithography, deep UV lithography, nanoimprint lithography or dip-pen lithography. The photolithographic technique can be, for example, contact aligner lithography, scanner lithography, or immersion lens lithography. Using a different mask, in case of photolithography, or mold, it may be possible to design particles having a number of predetermined regular, i.e. non-random shapes, such as spherical shape, square, rectangular, ellipse, disk and semi-spherical shapes. Patterning may be used to define lateral shape and dimensions of the particle, i.e. shape and dimensions of the particle in the cross section parallel to the surface of the substrate. When the formation of a porous layer precedes the patterning, the lateral dimensions of the fabricated particles are substantially the same as the lateral dimensions of the patterned features. When the patterning precedes the formation of a porous layer, the lateral dimensions of the fabricated particles may be larger than the lateral dimensions of the patterned features. Patterning allows one to produce particles having a predetermined regular, i.e. non-random, lateral shape. For example, in photolithographic patterning, masks of various shapes may be used to produce a desired predetermined shape, while in nanoimprint lithography, molds or stamps of various shape may be used for the same purpose. The predetermined non-random lateral shapes for the particles are not particularly limited. For example, the particles may have circular, square, polygonal and elliptical shapes.

Releasing

In some embodiments, the particles may be released from the wafer after the patterning and porous layer formation steps via electropolishing, which may involve applying a sufficiently large electrical current density to the wafer. Yet in some embodiments, the releasing of the particles from the wafer may involve a formation of an additional porous layer, which has a larger porosity than the already formed porous layer. This higher porosity layer will be referred to as a release layer. The release layer can have a porosity large enough so that it can be easily broken when desired using, for example, mechanical techniques, such as exposing the substrate to ultrasonic energy. At the same time, the release layer can be strong enough to hold the earlier formed porous layer intact with the substrate.

Surface Modification

Any of a number of techniques may be used to modify surface properties of the particles, i.e. surface properties of particle's outside surface, and/or surface properties of particle's pores. In many embodiments, surface modification of fabricated particles may be done while the particles are still intact with the substrate, before the particles are released. The types of surface modification for the particles may include, but are not limited to, chemical modification including polymer modification and oxidation; plasma treatment; metal or metal ion coating; chemical vapor deposition (CVD) coating, atomic layer deposition; evaporation and sputtered films, and ion implantation. In some embodiments, the surface treatment is biological for biomedical targeting and controlled degradation.

Because the surface modification of the particles may be performed before the particles are released from the substrates, asymmetrical surface modification is also possible. The asymmetric surface modification means a surface modification on one side of the particle is different than that on the other side of the particle. For example, one side of the surface of the particle may be modified, while the other side of the surface of the particle may remain unmodified. For instance, pores of the particles may be fully or partially filled with a sacrificial material, such as a sacrificial photoresist. Thus, only the outer surface of the particles is being treated during the surface modification. After selective removal of the sacrificial material, only the outer surface of the particles is modified, i.e. the pore surface of the particles remain unmodified. In some embodiments, the outer surface may be patterned by, for example, photolithography, so that one part of the outer surface may have one modification, while another part of the outer surface may have another modification. Exemplary surface modification protocols are presented further in the text. Embodiments described herein are further illustrated by, though in no way limited to, the following working examples.

EXAMPLE 1

Fabrication of Porous Silicon Particles.
Electropolishing Release

Figure 1A:
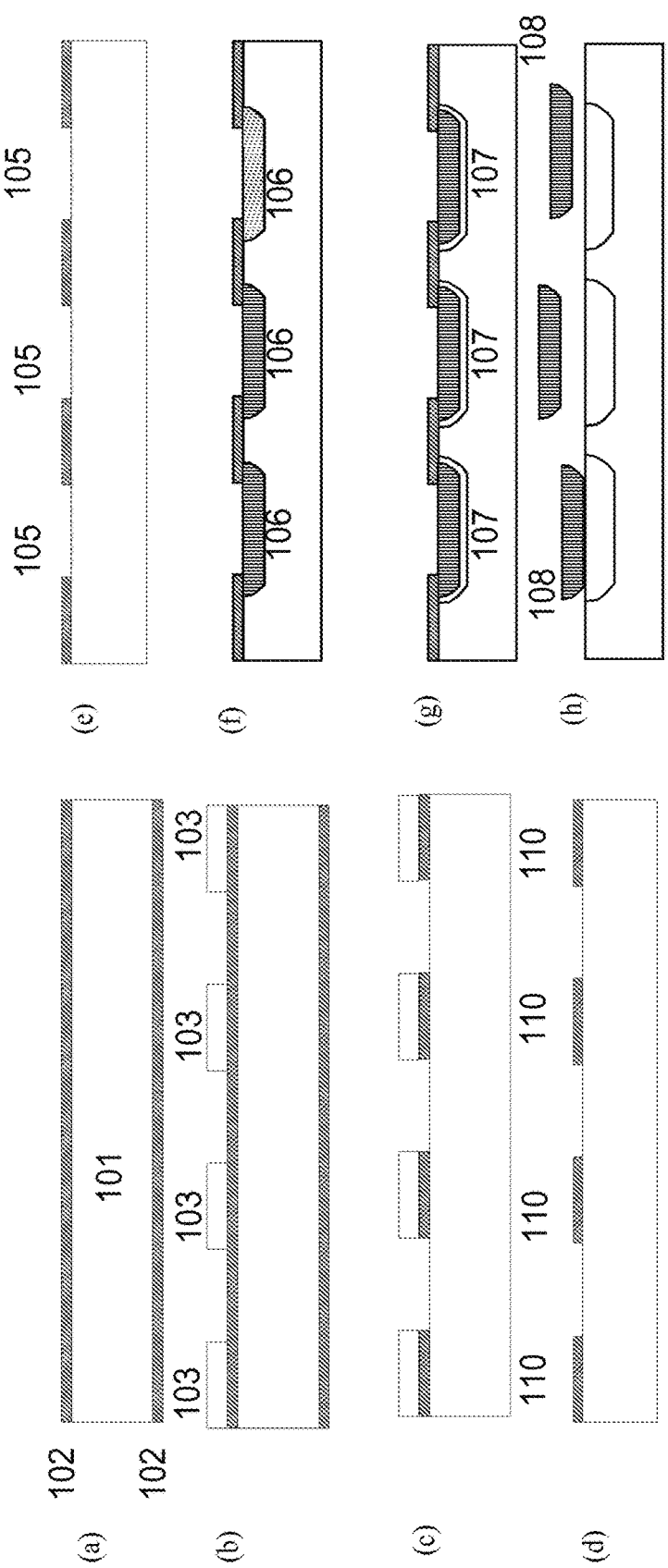
Figure 1B:
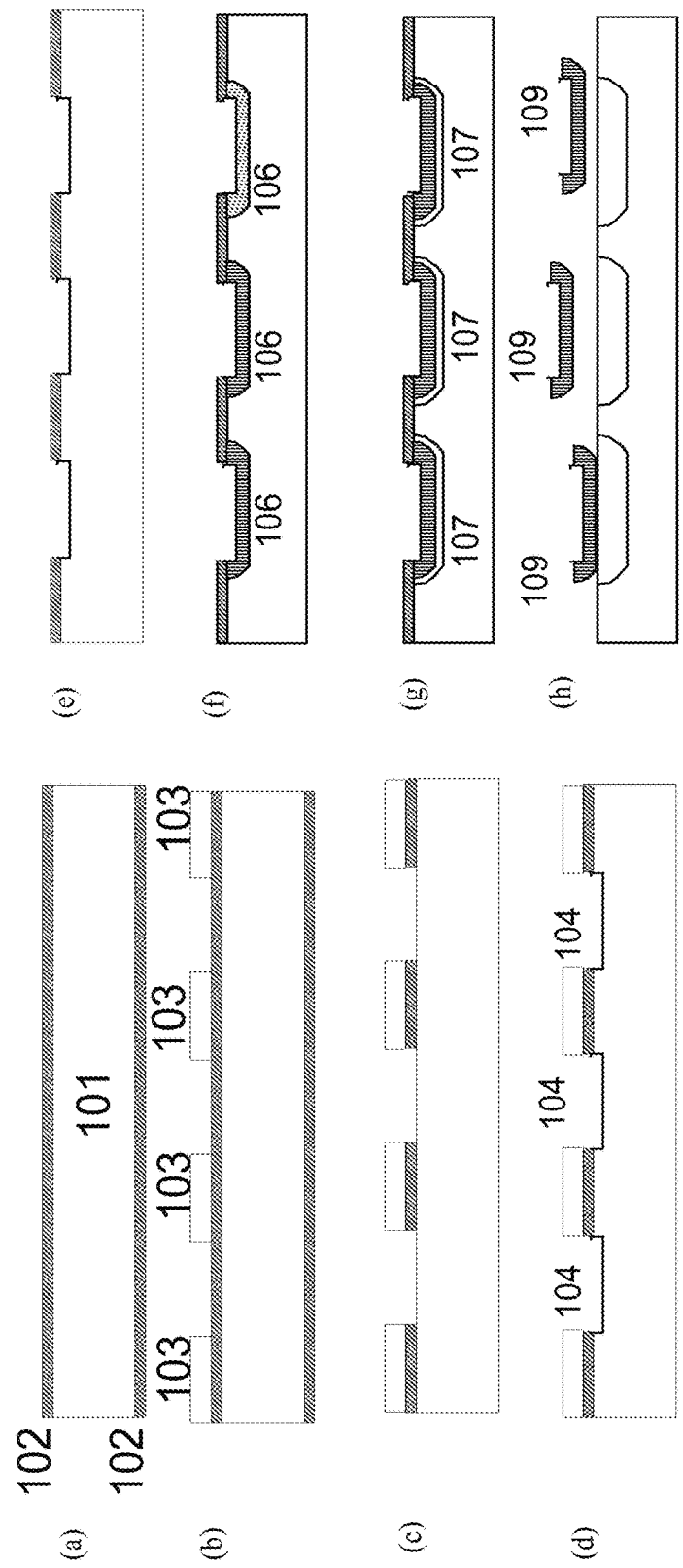

In a process schematically illustrated in FIGS. 1A and 1B, particles patterning precedes the porous layer formation and release of the particles is performed via electropolishing. The fabrication starts with obtaining a silicon wafer 101. The surface of the wafer 101 is roughened by a treatment, such as KOH dipping or reactive-ion etching (RIE). The roughening of the surface helps in removing or preventing the formation of the nucleation layer on the surface. A protective layer 102 is then deposited on at least one surface of the wafer 101 to protect the wafer from electrochemical etching in HF based solution. The protective layer 102 is a material resistant to electrochemical etching in HF solution. Examples of such materials include silicon nitride or photoresist.

Then the protective layer 102 is patterned. FIGS. 1A and 1B illustrate patterning of the protective layer by a lithographic technique. As FIGS. 1Ac and 1Bc, a layer of a resistant material 103 is deposited over the protective layer 102. The resistant material is a material that does not get removed under the conditions, for which the protective layer gets removed. One example of such a material is a photoresist. The undesired area of the protective layer 102 on the front surface of the wafer is removed as well as the protective layer on the back side on the wafer, see FIGS. 1Ac and 1Bc. The resistant material 103 is removed as well, see FIG. 1Ad. The protective layer is patterned is such a way so that the spaces between the patterned areas 110 of the protective layer define the shape and dimensions of the fabricated particles.

In some cases, as illustrated in FIG. 1Bd, trenches are formed in the spaces 104 between the patterned areas 110 of the protective layer. The trenches are formed by a dry etching technique (i.e., RIE). The depth and shape of trenches are used to define the cross section of the particles perpendicular to the surface of the substrate and thus the shape of the particles. The depth and shape of the trenches are also to control mechanical and/or porous properties of the fabricated particle.

A porous layer 106 is formed in and around the spaces unprotected by the patterned areas 110 of the protective layer, see FIGS. 1Af and 1Bf. To form the porous layer 106, the wafer is exposed to a solution that includes HF and optionally a surfactant, such as an ethanol, under a DC electrical current, a value of which is selected to generate pores of a desired size. If a nucleation layer 105 is undesirable, a larger DC current is applied prior to applying the DC current corresponding to the desired pore size, see FIG. 1Ae.

The formed porous layer 106 has two different pore orientations in the region unprotected by the patterned areas 110 and in the region of the substrate under the protective layer areas 110. The former has pores oriented perpendicular or substantially perpendicular to the surface of the substrate, while the latter has pores oriented parallel to the surface of the substrate or angled to the surface with an angle substantially different from 90°.

The particles 108 or 109 are released via electropolishing, which form a gap 107 underneath the porous layer 106, see FIGS. 1Ag,h and 1Bg,h. The remaining protective layer is then removed. The particles are collected in the solution by a number of techniques, including filtration. The particles 109 have a trench formed in them that define their shape and their mechanical and porous properties. For example, a part of the particle 109 under the trench have a pore size and porosity that are different from a pore size and porosity at the sides of the particle 109, i.e. non-trench part of the particle 109.

EXAMPLE 2

Fabrication of Porous Silicon Particles. Release Via Formation of the Second Porous Layer In a process schematically illustrated in FIGS. 2A and 2B, particles patterning precedes a porous layer formation and release of the particles is performed via a formation of a second porous layer. The fabrication process starts with obtaining of a silicon wafer 201. As in the previous protocol, a surface of the wafer 201 is roughened by KOH dipping or RIE. As in Example 1, a protective layer 202 is then deposited on the wafer to protect the wafer from electrochemical etching in HF based solution, see FIG. 2Aa. As in Example 1, the protective film 202 is then patterned using a lithographic technique, see FIGS. 2Ab,c and 2Bb,c. As in Example 1, the patterning involves deposition of a resistant film 203, see FIGS. 2Bb and 2Ab. The undesired area of the protective film on the front side of the wafer is removed, as well as the protective film on the back side of the wafer 201, see FIGS. 2Bc and 2Ac. As in Example 1, the protective layer 202 is patterned is such a way so that the spaces between the patterned areas 210 define the shape and dimensions of the fabricated particles.

Figure 2A:
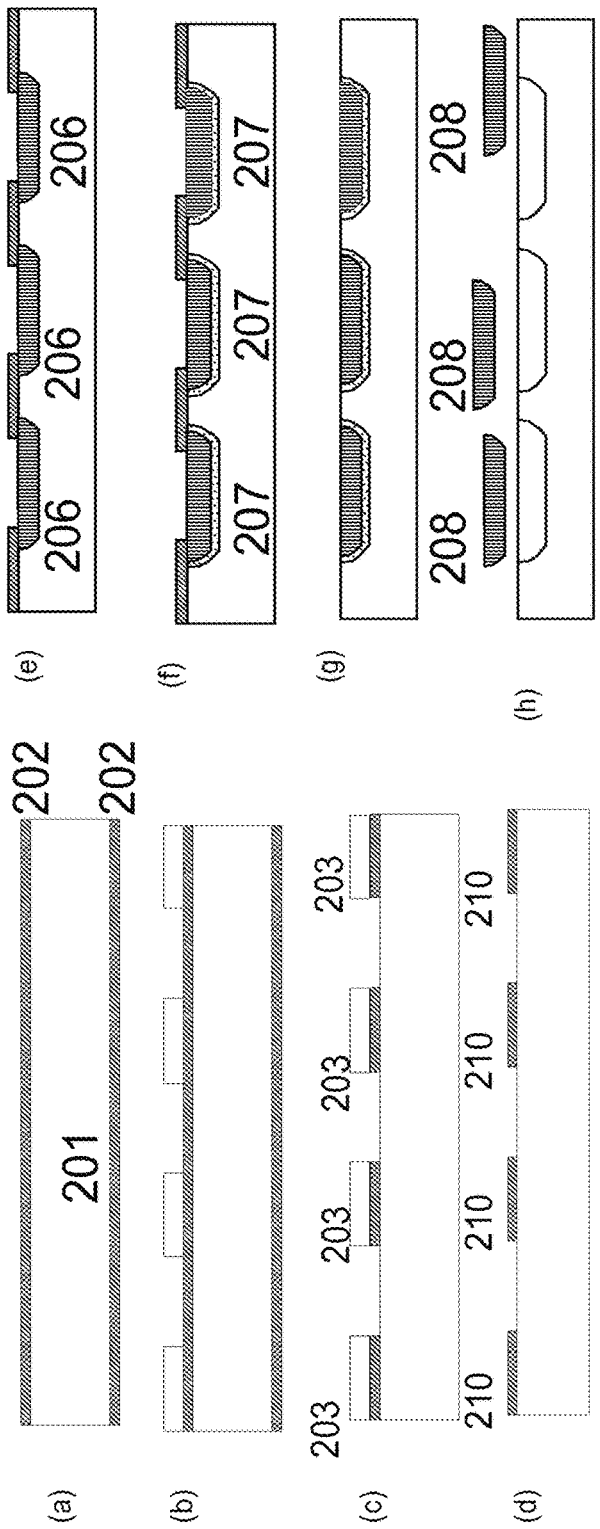
Figure 2B:
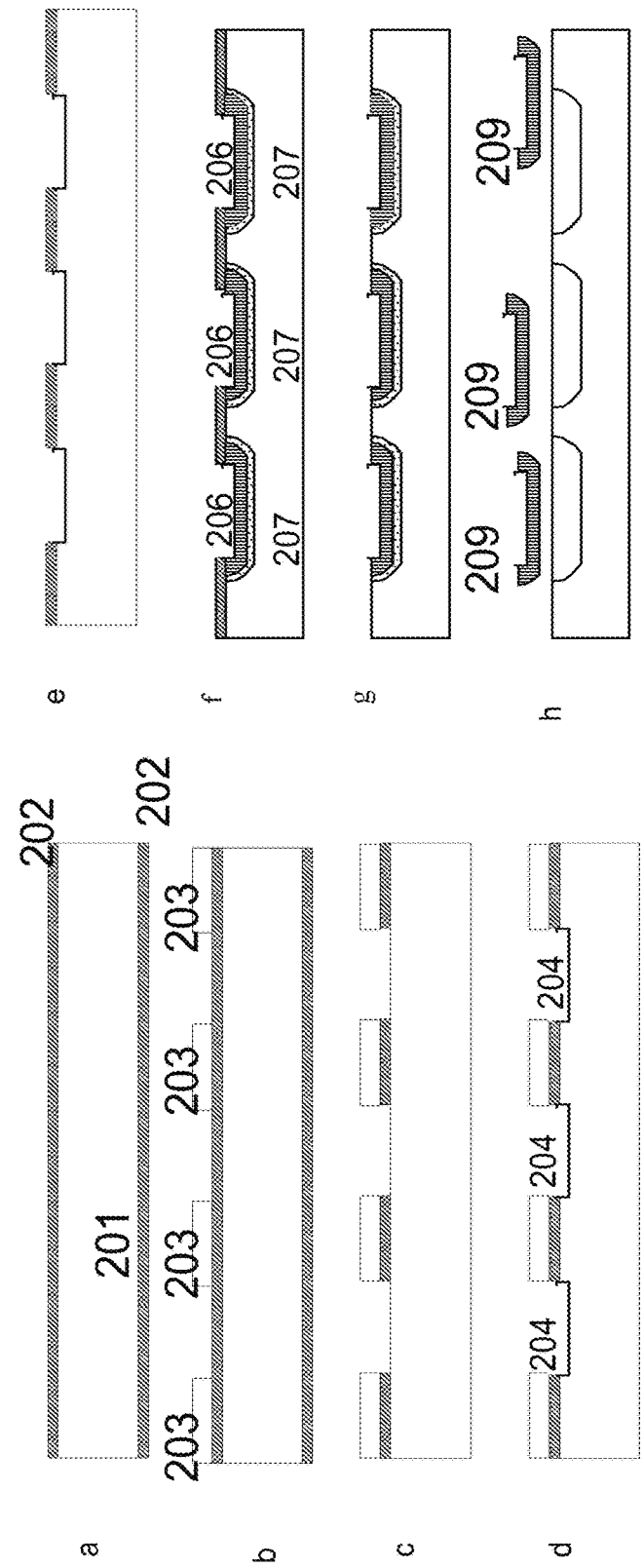

In some cases, as illustrated in FIG. 2Bd, trenches 204 are formed in the spaces between the patterned areas 210 of the protective layer. The trenches are formed by dry etching, such as RIE. The depth and shape of trenches are used to define the cross section of the particles perpendicular to the surface of the substrate and thus the shape of the particles. The depth and shape of the trenches are also used to control mechanical and porous properties of the formed particles.

A porous layer 206 is formed in and around the spaces unprotected by the patterned areas 210 of the protective layer, see FIGS. 2Ae,f and 2Bf. To form the porous layer 206, the wafer is exposed to a solution that includes HF and optionally a surfactant under a DC electrical current, a value of which is selected to generate pores of a desired size. If a nucleation layer is undesirable, a larger DC current is applied prior to applying the DC current corresponding to the desired pore size.

The formed porous layer 206 has two different pore orientations in the region unprotected by the patterned areas 210 and in the region of the substrate under the protective layer areas 210. The former has pores oriented perpendicular or substantially perpendicular to the surface of the substrate, while the latter has pores oriented parallel to the surface of the substrate or angled to the surface of the substrate with an angle substantially different from 90°.

After the formation of the porous layer 206, a larger electrical current is applied to form a second porous layer 207 that has a larger porosity than the first layer, see FIGS. 2Bf and 2Af. This larger electrical current is selected to be such that the second porous layer 207 is fragile enough for mechanical break-down, but still holds the particles in place.

If the nucleation layer has not been removed earlier, it is removed at this stage by using a dry etching technique, such as RIE. The patterned areas 210 of the protective film is then removed, see FIGS. 2Ag and 2Bg. The particles kept in the wafer 201 by the second porous layer 207 is then chemically modified, if desired.

The particles 208 or 209 are released from the wafer 201 in a solution by breaking the second porous layer 207, which is done for example by mechanical means such as exposing the wafer to ultrasonic vibrations, see FIGS. 2Ah and 2Bh. The particles 209 have a trench formed in them that define their shape and their mechanical and porous properties. For example, a part of the particle 209 under the trench has a pore size and porosity that are different from a pore size and porosity at the sides of the particle 209, i.e. non-trench part of the particle 209.

The shapes of particles fabricated in Examples 1 and 2 are semispherical, bowl, frustum, etc., depending on the etching condition. For example, for the bowl shape, a depth of the bowl depends on a depth of the trench formed into the particle patterns prior to electrochemical wet etching.

EXAMPLE 3

Fabrication of Porous Silicon Particles

Figure 3:
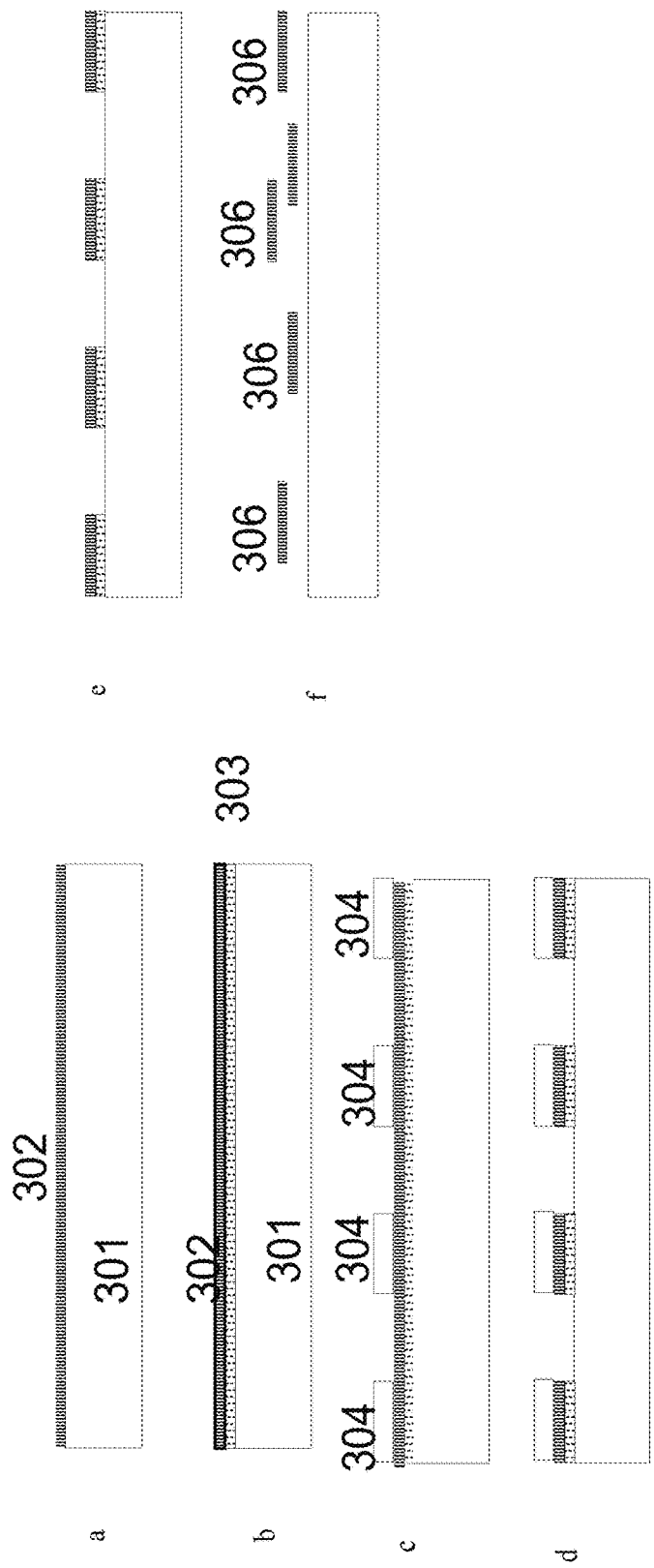

In a process schematically illustrated in FIG. 3, porous layer formation precedes particles patterning. The process starts with obtaining a silicon wafer 301. To form a porous layer 302, the wafer is then exposed to a solution that includes HF and optionally surfactant, under a DC electrical current, a value of which is selected to obtain a desired size of pores in the layer 302, see FIG. 3a. A larger electrical current is subsequently applied to form a second porous layer 303 in the substrate 301 underneath the first porous layer. This larger electrical current is selected so that the second porous layer 303 has a larger porosity than the first porous layer 302, see FIG. 3b. Preferably, this larger electrical current is selected to be such that the porous layer 303 is fragile enough for mechanical break-down if necessary, but, at the same time, holds formed particles in place within the wafer.

After the formation of the second porous layer, particles are patterned. For example, a photoresist layer is deposited onto the porous silicon film 301. The photoresist layer is then patterned to define particles. For example, in FIG. 3, patterned areas 304 of the photoresist layer (FIG. 3c) define the particles. The undesired area of the porous silicon layer 302, i.e. the areas of the porous layer 302 not covered by the patterned areas 304 of the photoresist layer, is removed by, for example, dry etching, such as RIE, see FIG. 3d. The patterned areas 304 of the photoresist layer is then removed.

The particles kept in the wafer 301 by the second porous layer 303, see FIG. 3e, is then chemically modified, if desired. The particles 306 are released from the wafer 301 in a solution by breaking the second porous layer 302, which is done for example by mechanical means, such as exposing the wafer to ultrasonic vibrations, see FIG. 3f.

EXAMPLE 4

High Yield Fabrication of Porous Silicon Particles I

The process of Example 3 is transformed to a multilayer method, which allows for producing a high yield of fabricated particles. The method starts with obtaining a silicon wafer 401. The wafer 401 is then exposed to HF/surfactant solution, and DC electrical current is applied for certain time to form a first porous silicon layer 402, see FIG. 4a. Then a larger electrical current is applied to form a second porous layer 403 with larger porosity as a release layer. This larger current is selected to be such that the second porous layer 403 is fragile enough for mechanical break-down, but, at the same time, holds the particles in the wafer 401.

Figure 4:
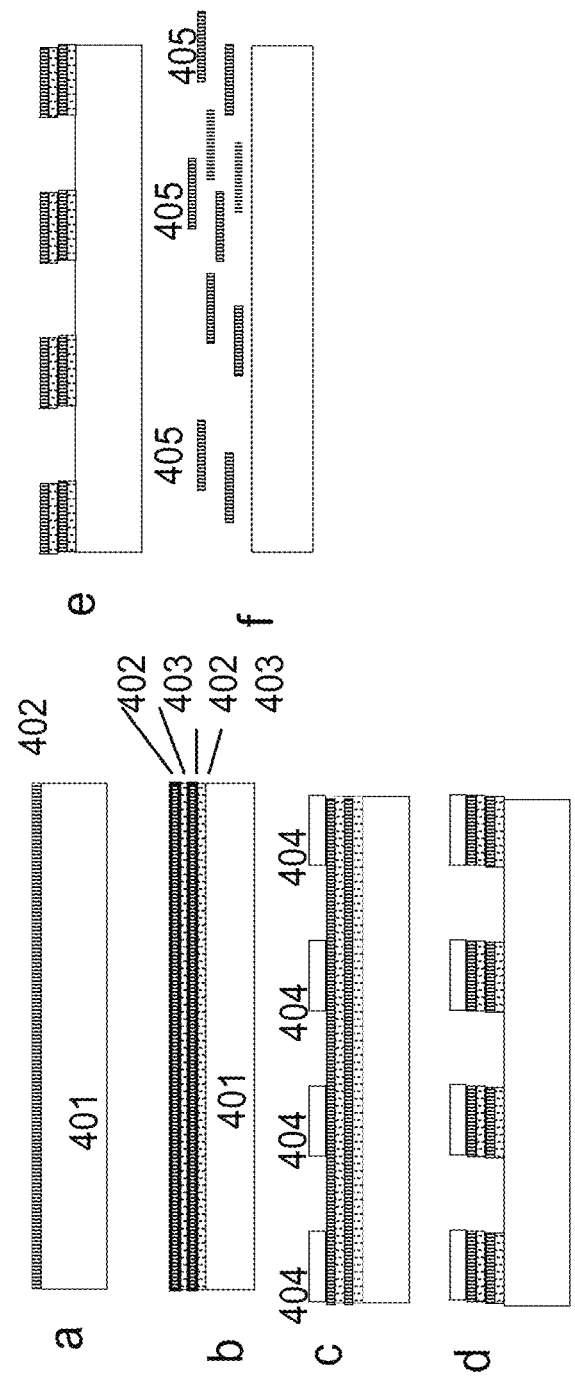

The steps of forming a stable porous layer, such as the first porous layer 402, and forming a breakable release porous layer, such as the second porous layer 403, is repeated to form a periodical layered structure. For example, FIG. 4b shows such a periodic structure, in which stable porous layers 402 are separated by breakable release layers 403. Patterning of particles is then performed.

For example, a masking layer, such as a metal film, is deposited on the top first porous layer 402. A photoresist layer is placed on top of the masking film. In the case when the metal masking film is not deposited, the photoresist is placed directly on the top first porous layer 402. Then, a lithographic technique is applied to pattern the photoresist layer. As shown in FIG. 4c, the patterned photoresist layer includes patterned photoresist areas, which defines shape and dimensions of fabricated particles. An undesired area of the periodical porous structure, i.e. the area of the periodical structure not covered by the patterned photoresist areas 404, is then removed to form stacks 406 toped by the patterned photoresist areas 404, see FIG. 4d. Then, the photoresist film and/or the masking film is removed from the top of the stacks 406, see FIG. 4e, by using piranha solution (1 volume $H_2O_2$ and 2 volumes of $H_2SO_4$). If desired, particles 405, which are formed from portions of stable porous layers and which are kept in the stacks 406 by releasable porous layers are then chemically modified. A release of the particles 405 from the stacks 406 into a solution are performed by mechanical means, such as exposing the wafer 401 with the stacks 406 to ultrasonic vibrations, see FIG. 4f.

EXAMPLE 5

High Yield Fabrication of Porous Silicon Particles II

The present example presents an alternative method for a high yield fabrication of porous silicon particles. Starting from a silicon wafer 501, a protective layer is deposited on the wafer to protect the wafer from anisotropic etching, such as Deep RIE. The protective layer is a silicon dioxide film or a photoresist film. The protective film is patterned to form patterned areas 502 of the protective layer that define a cross section shape and dimensions of particles to be fabricated, see FIG. 5a. This initial patterning of the protective layer is performed similarly to the patterning of the protective layer illustrated in FIG. 1A (a)-(d).

Figure 5:
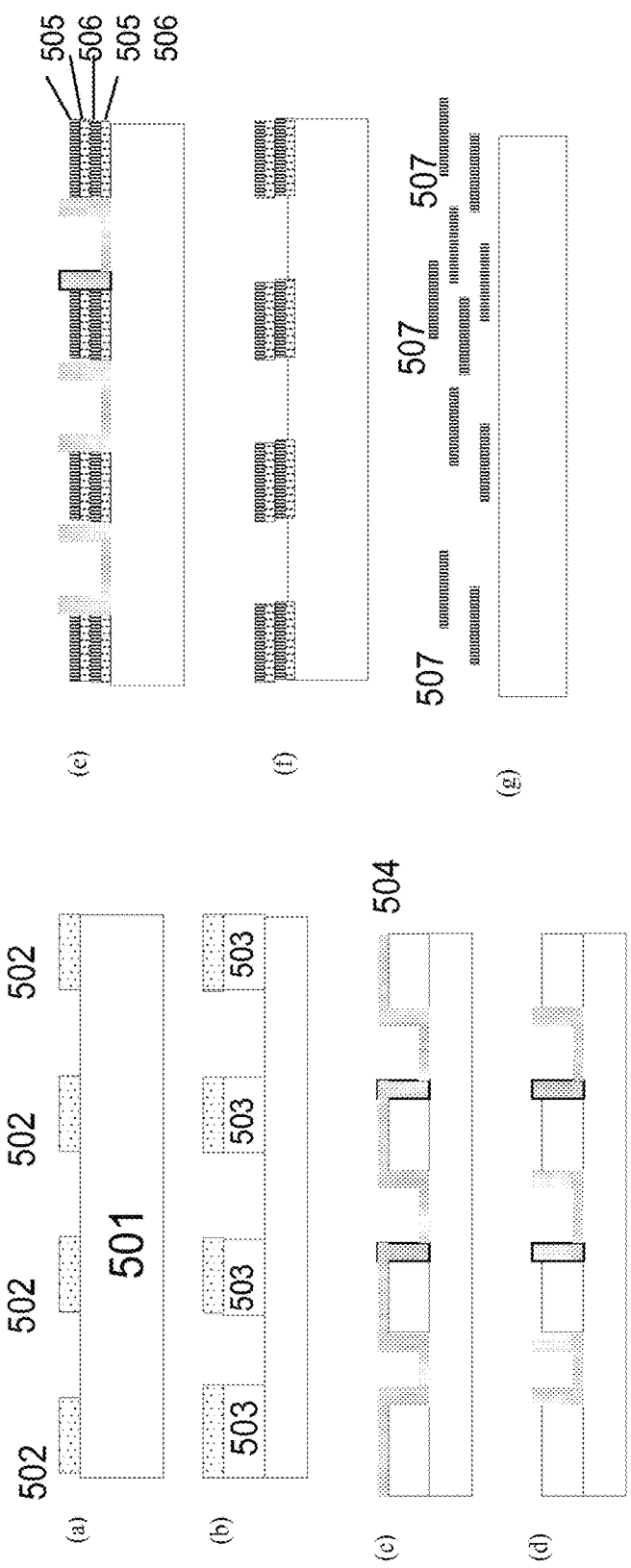

An anisotropic etching technique is then applied to unprotected areas of the wafer to form pillars 503 underneath the patterned areas 502 of the protective film, see FIG. 5b. The protective film 502 on the top of the pillars 503 is then removed. Then, a second protective layer 504 is deposited over the pillars 503 and in the etched areas 508 between the pillars 503, see FIG. 5c. The second protective layer 504 is such that it protects the wafer from electrochemical etching in HF based solution. For example, the second protective layer 504 is a silicon nitride film or a photoresist film. The tops of the pillars 503 is then exposed by removing portions of the second protective layer 504 by, for example, etching or planation. Preferably, after such removal, the second protective layer 504 remains intact on the sides and at the bottom of the etched areas 508, see FIG. 5d.

After that, the wafer with the patterned pillars are exposed to HF-based solution under applied DC electrical current to form a first porous layer 505, which is a stable porous layer from which the particles are formed. The applied DC current is selected to form pores with a size desired in the particle. After that, a larger electrical current is applied to form a second porous layer 506, which is a release porous layer with a larger porosity than the first porous layer 505. This larger electrical current is selected to be such so that the release porous layer is, on one hand, fragile enough for mechanical break-down, and, on the other, it is strong enough to hold the particles in place before the release. The steps of formation a stable porous layer, such as the layer 505 and formation of a release layer, such as a layer 506 is repeated a desired number of times to form a periodical layered structure in the pillars 503. For example, FIG. 5(e) shows a periodical structure 509 formed by interchanging stable porous layers 505 and release porous layers 506.

Upon the formation of the periodic stack structure 509, the remaining second protective layer 504 is removed, see FIG. 5f.

If desired, particles 507, which are formed from portions of stable porous layers 505 and which are kept in the periodic stack structures 509 by releasable porous layers 506, are then chemically modified. A release of the particles 507 from the stacks 509 into a solution is performed by mechanical means, such as exposing the wafer 501 with the stacks 509 to ultrasonic vibrations, see FIG. 5g.

In the above method, the step of forming large porosity release layers is replaced by electropolishing. In this case, the formed periodic structures include interchanging stable porous layers and gaps formed by electropolishing, instead of the release porous layer. The stable porous layers hold intact with the wafer by the remaining second protective layer 504. In such a case, the release of the particles formed from the stable porous layers are performed by removing the remaining second protective layer. Prior to the release, the particles are chemically modified while still intact with the wafer.

Surface Modification Protocols

Below are provided exemplary protocols, which are used for surface modification of silicon particles by oxidation, silanization and attaching targeting moieties, such as antibodies.

Oxidation of Silicon Microparticles

Silicon microparticles in IPA are dried in a glass beaker kept on a hot plate (80-90° C.). Silicon particles are oxidized in piranha (1 volume $H_2O_2$ and 2 volumes of $H_2SO_4$). The particles are sonicated after $H_2O_2$ addition and then acid is added. The suspension is heated to 100-110° C. for 2 hours with intermittent sonication to disperse the particles. The suspension is then washed in DI water unil the pH of the suspension is about 5.5-6. Particles are then transferred to appropriate buffer, IPA (isopropyl alcohol) or stored in water and refrigerated until further use.

Silanization i) Oxidation. Prior to the silanization process, the oxidized particles are hydroxylated in 1.5 M $HNO_3$ acid for approximately 1.5 hours (room temperature). Particles are washed 3-5 times in DI water (washing includes suspending in water and centrifuging, followed by the removal of supernatant and the repeating of the procedure).

ii) APTES Treatment. The particles are suspended in IPA (isopropyl alcohol) by washing them in IPA twice. Then the particles are suspended in IPA solution containing 0.5% (v/v) of APTES (3-aminopropyltriethoxysilane) for 45 minutes at room temperature. The particles are then washed with IPA 4-6 times by centrifugation and stored in IPA refrigerated. Alternatively, the particles are aliquoted, dried and stored under vacuum and desiccant till further use.

iii) MPTMS Treatment. The particles are hydroxylated in HNO3 using the same procedure as above. After the washes with water and IPA, the particles are silanized with MPTMS (3-mercaptopropyltrimethoxysilane) 0.5% v/v and 0.5% v/v in IPA for 4 hours. The particles are then washed with IPA 4-6 times, and then stored in IPA refrigerated or aliquoted, dried, and stored under vacuum and desiccant.

iv) Conjugation of Antibodies. Microparticles are modified with APTES and/or MPTMS as described above. Sulfo-SMCC, a water soluble analog of succinimidyl 4-N-maleimidomethyl cyclohexane-1-carboxylate (SMCC) crosslinker, are used to crosslink the particles with the anti-VEGFR2 antibody. The total number of particles used for conjugating both APTES and MPTMS particles with the anti-VEGFR2 are about $7.03 \times 10^6$. The particles are washed and centrifuged in phosphate buffer containing 0.5% Triton X-100 6 times followed by 4 washes in plain phosphate buffer and then read on the plate reader.

Immobilization of antibodies, such as IgG, EGFR, VEGFR, to nanoporous silicon particles via a chemical scaffold by surface sialinization followed by subsequent coupling methods involving readily available protein cross-linking agents capable of covalently linking these antibodies has been experimentally demonstrated.

Surface Modification with APTES

In an exemplary surface modification, porous silicon particles are hydroxylated in 1.5M $HNO_3$ for 1 hr. Amine groups are introduced on the surface by silanization with a solution comprising 0.5% v/v 3-aminopropyltriethoxysilane (APTES) in isopropanol (IPA) for 30 min at room temperature. Thiol groups are coated on the surface using 0.5% v/v 3-mercaptopropyltrimethoxysilane (MPTMS) and 0.5% v/v $H_2O$ in IPA. APTES-coated and MPTMS-coated particles are suspended in phosphate-buffered saline (PBS) and reacted with the crosslinker 1 mM N-succinimidyl-S-acetyl-thioacetate (SATA), 1 mM sulfosuccinimidyl 4-(N-maleimidomethyl)cyclohexane-1-carboxylate (Sulfo-SMCC), 1 mM N-Succinimidyl[4-iodoacetyl]aminobenzoate (Sulfo-SIAB), or 1 mM succinimidyl 6-(3-[2-pyridyldithio]-propionamido)hexanoate (SPDP) for 1 h at room temperature. Then the antibodies are bioconjugated on the particles.

EXAMPLE 6

Fabrication of "Large Pore" Silicon Particles

Figure 6:
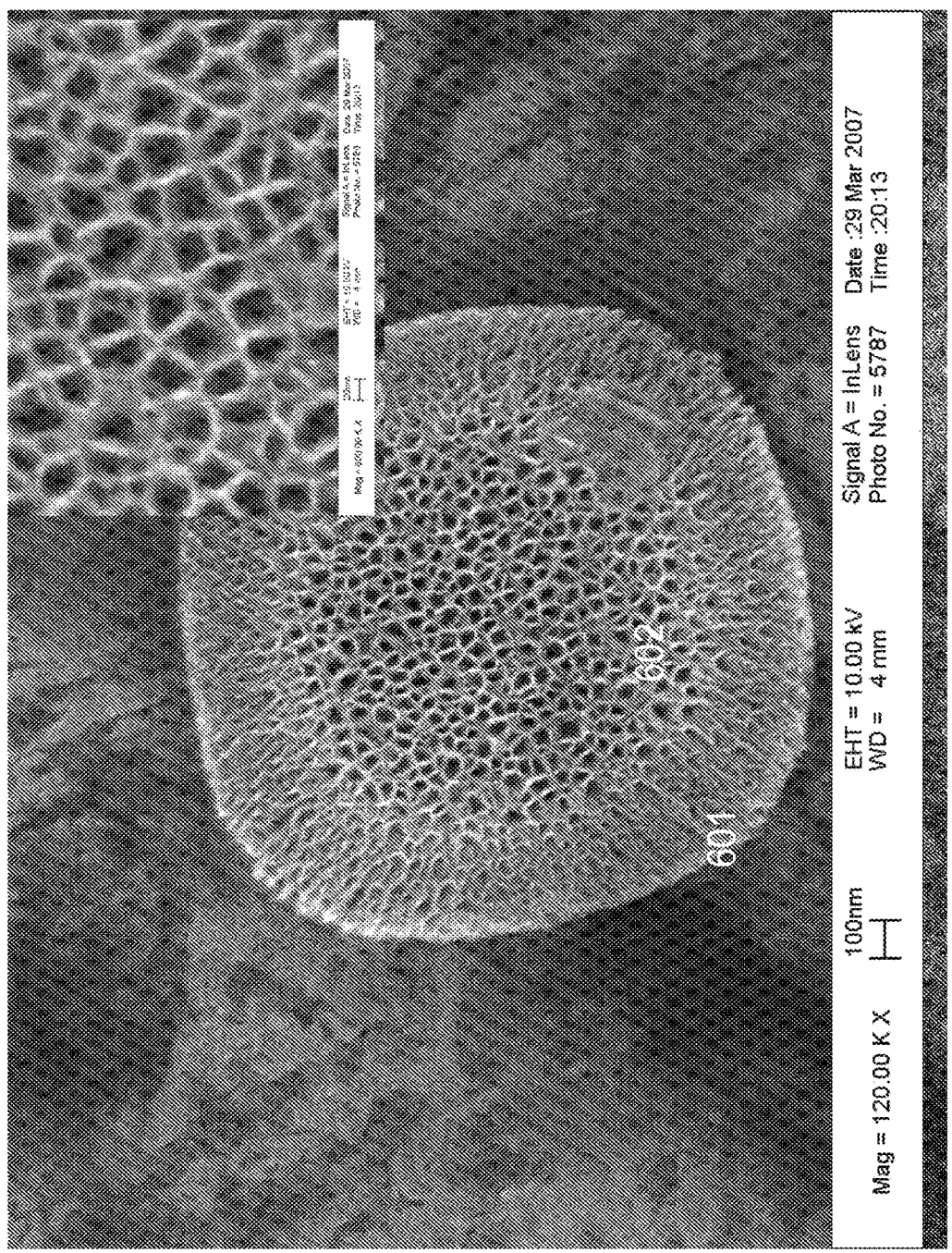
FIG. 6 is a Scanning Electron Microscope (SEM) image of a bottom view of a 1.2 μm of porous silicon particle. The inset shows a close view of ~30 nm pores in the central region of the particle.

FIG. 6 shows a scanning electron image of a 1.2 μm silicon porous particle fabricated as follows. Heavily doped p++ type (100) wafer with resistivity of 0.005 ohm-cm (Silicon Quest Inc) was used as the substrate. A 200 nm layer of silicon nitride was deposited by Low Pressure Chemical Vapor Deposition (LPCVD) System. Standard photolithography was used to pattern the 1 μm circular particle patterns using EVG 620 aligner (vacuum contact). The silicon nitride was then selectively removed by reactive ion etching (RIE). The silicon nitride on the back side of the wafer was removed by RIE. 300 nm silicon trenches were etched into silicon in exposed particle patterns. The photoresist was removed with piranha ($H_2SO_4:H_2O_2=3:1$ by volume). Aluminum film was coated on the backside of the wafer. The wafer was then placed in a home-made Teflon® cell for electrochemical etching. The nanopores were formed in the mixture of hydrofluoric acid (HF) and Ethanol (3:7 v/v) with applied current density of 80 mA/cm$^2$ for 25 second. A release high porosity layer was formed by applying the current density of 400 mA/cm$^2$ for 6 second. After removing the nitride layer by HF, particles were released in IPA by exposure to ultrasound for 1 minute. The IPA containing porous silicon particles was collected and stored.

The morphology of the silicon particles was determined using LEO 1530 scanning electron microscopy. Particles in IPA were directly placed on aluminum SEM sample stage and dried. The SEM stages with particles are loaded into LEO 1530 sample chamber. The acceleration voltage of electron beam is 10 kV, and working distance is about 5 mm.

The SEM image in FIG. 6 shows a bottom view, i.e. a view of a side, which was away from a front surface of the wafer during the fabrication, of a particle having a circular (1.2 □m in diameter) shape parallel to the surface of the wafer. The overall 3 dimensional shape of the particle in FIG. 6 is semispherical. The image in FIG. 6 shows regions 601 and 602, which correspond to pores parallel or angled to the surface and pores perpendicular to the surface, respectively. The pore size in the center of particle is about 30 nm. The resulting particles are bigger than the original patterns because the porous layer penetrates beneath and into the protected area of the substrate during electrochemical etching.

EXAMPLE 7

Fabrication of Oval Shaped "Large Pore" Silicon Particles

Figure 7:
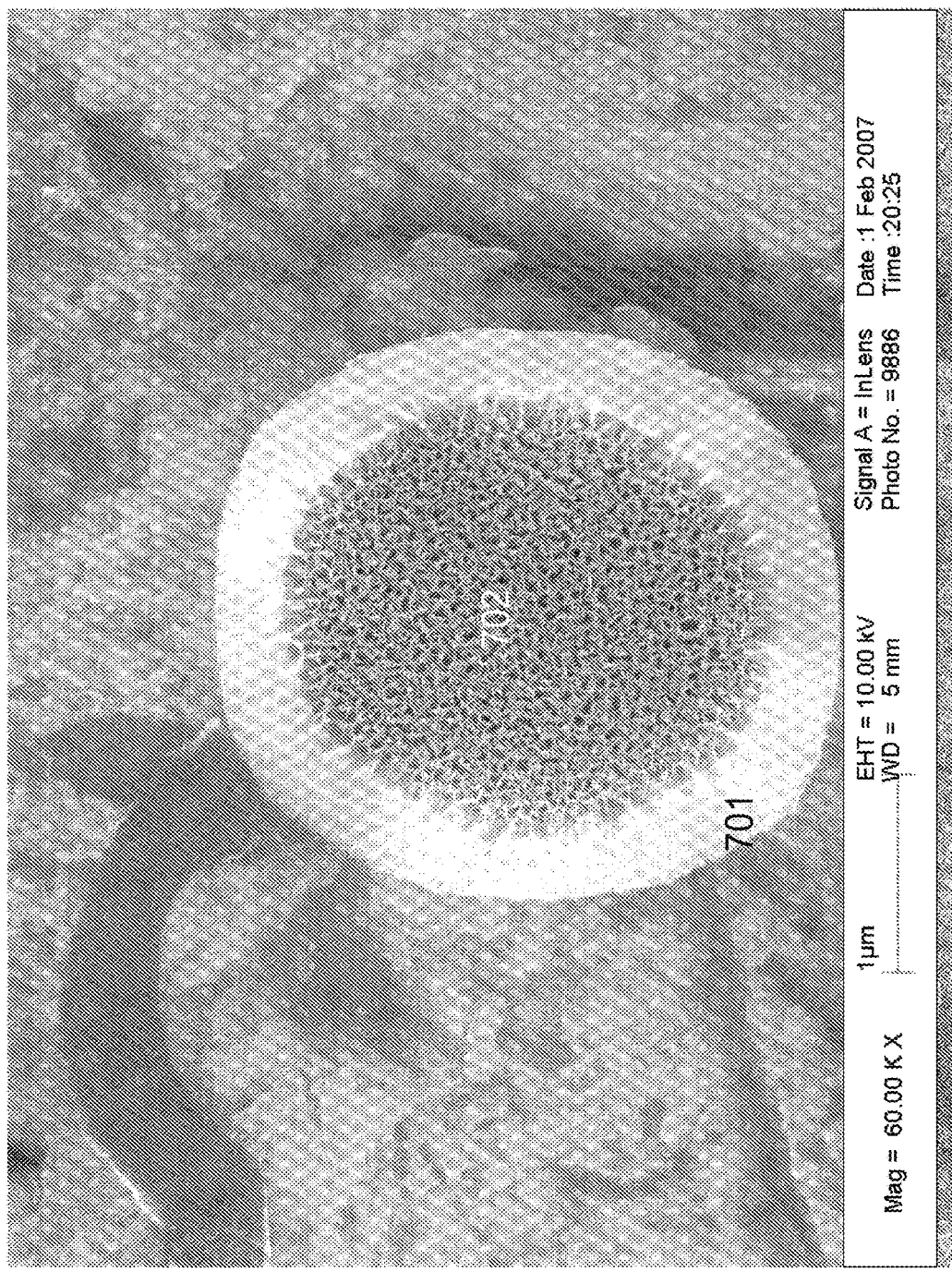
FIG. 7 is an SEM image of a top view of a 3 μm silicon particle having an oval cross section.

FIG. 7 shows an SEM image of a silicon particle having an oval cross section. The particle was fabricated as follows. Heavily doped p++ type (100) wafer with resistivity of 0.005 ohm-cm (Silicon Quest Inc) was used as the substrate. A 200 nm layer of silicon nitride was deposited by Low Pressure Chemical Vapor Deposition (LPCVD) System. Standard photolithography was used to pattern the 2 μm oval shaped particles using EVG 620 aligner. The nitride was then selectively removed by reactive ion etching (RIE). The silicon nitride on the back side of the wafer was removed by RIE. 600 nm silicon trenches are etched into silicon in exposed particle patterns. The photoresist was removed with piranha ($H_2SO_4$:$H_2O_2$=3:1 by volume). The wafer was then placed in a home-made Teflon® cell for electrochemical etching. The etching solution was a mixture of hydrofluoric acid (HF) and ethanol (3:7 v/v). A high density electrical current of 400 mA/cm2 was applied for 1 second to remove a nucleation layer. Then the nanopores were formed with applied current density of 80 mA/cm$^2$ for 25 second. A high porosity release layer was formed by applying a current density of 400 mA/cm$^2$ for 6 second. After removing the nitride layer by HF, particles were released in IPA by ultrasound for 1 minute. The IPA solution containing porous silicon particles was collected and stored. A drop of the IPA solution containing the fabricated particles was directly placed on aluminum SEM sample stage and dried. The SEM image was measured using a LEO 1530 scanning electron microscope. The acceleration voltage of electron beam is 10 kV, and working distance is about 5 mm. The SEM image in FIG. 7 shows the top view of the resulting particle. The particle has a region 701, in which pores are parallel or angled to the surface, and a region 702, in which pores are perpendicular to the surface.

EXAMPLE 8

Fabrication of "Small Pore" Silicon Particles

Figure 8:
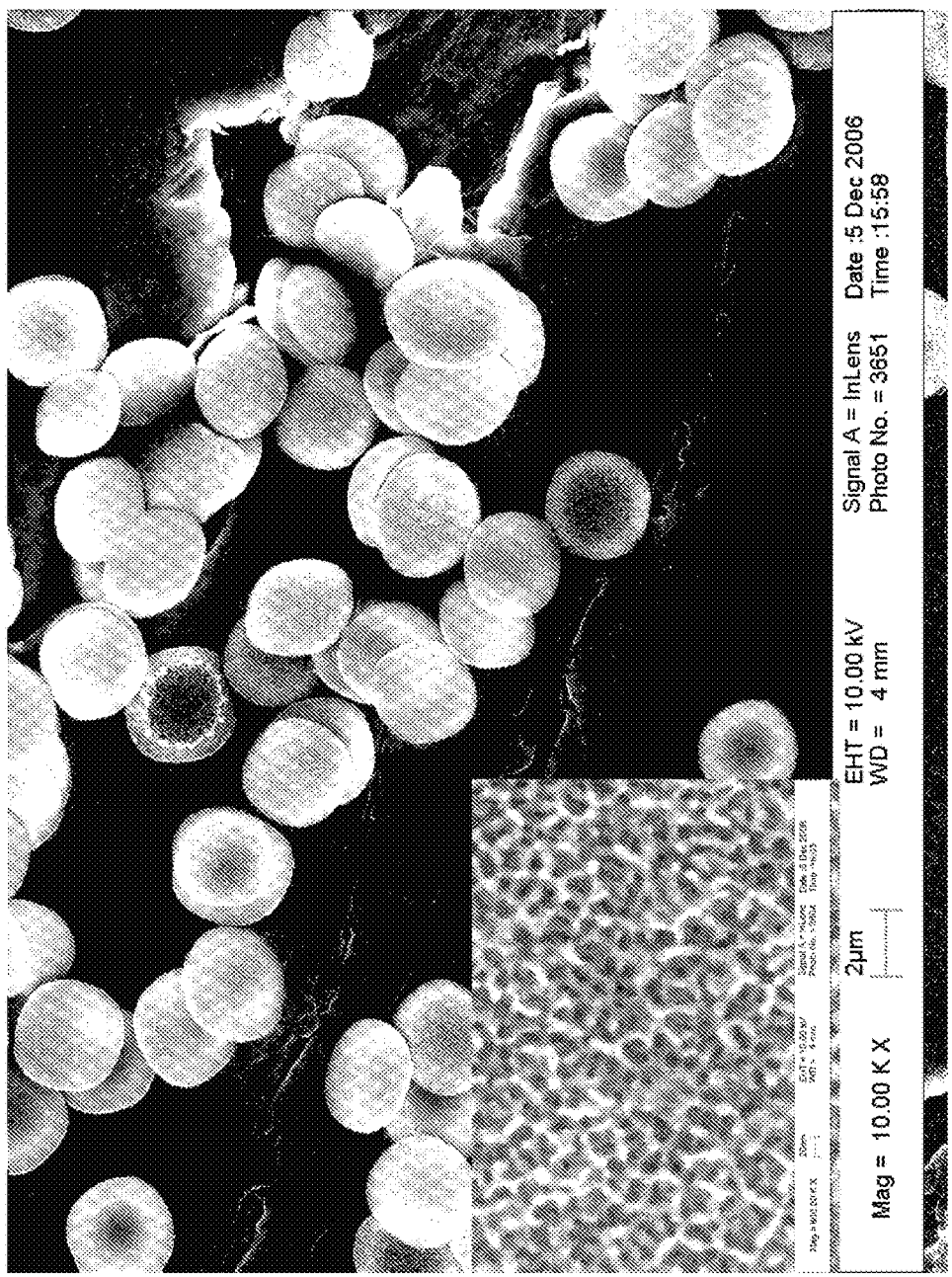
FIG. 8 is an SEM image of 3.1 μm particles that have a semispherical shape. The inset shows a detailed view of a surface of one of the particles with <10 nm pores.

FIG. 8 is an SEM image showing 3.1 μm particles that have a semispherical shape. The particles were fabricated as follows. Heavily doped p++ type (100) wafer with resistivity of 0.005 ohm-cm (Silicon Quest Inc) was used as a substrate. A 200-350 nm layer of silicon nitride was deposited on the substrate by Low Pressure Chemical Vapor Deposition (LPCVD) System. Photolithography was used to pattern the 2 μm circular particle patterns. The nitride was then selectively removed by reactive ion etching (RIE). The silicon nitride on the back side of the wafer was removed by RIE. The photoresist was removed with piranha ($H_2SO_4$: $H_2O_2$=3:1 by volume). The wafer was then placed in a home-made Teflon® cell for electrochemical etching. The nanopores were formed in a mixture of hydrofluoric acid (HF) and Ethanol (1:1 v/v) with a current density of 6 mA/cm$^2$ applied for 1 min 45 second. A high porosity release layer was formed by applying a higher current density of 320 mA/cm$^2$ for 6 second in the mixture of hydrofluoric acid (HF) and Ethanol (2:5 v/v). After removing the nitride layer by HF, the particles were released by exposing the substrate to ultrasonic vibrations for 1 minute. A drop containing particles in IPA was directly placed on an aluminum SEM sample stage and dried. The SEM image was measured using a LEO 1530 scanning electron microscope. The acceleration voltage of electron beam is 10 kV, and working distance is about 5 mm. The SEM image in FIG. 8 shows the fabricated particles. The inset demonstrates that the fabricated particle have a pore size of less than 10 nm.

EXAMPLE 9

Fabrication of "Large Pore" Silicon Particles

FIG. 10 shows an SEM image of 3.2 μm silicon particles with 500 nm trench. The particles were fabricated as follows. Heavily doped p++ type (100) wafer with resistivity of 0.005 ohm-cm (Silicon Quest Inc) was used as a substrate. A 100 nm layer of low stress silicon nitride was deposited on the substrate by Low Pressure Chemical Vapor Deposition (LPCVD) System. Standard photolithography was used to pattern the 2 μm circular particle patterns using EVG 620 aligner. The nitride was then selectively removed by reactive ion etching (RIE). The silicon nitride on the back side of the wafer was removed by RIE. 500 nm silicon trenches were etched into silicon on the exposed particle patterns by RIE. The photoresist was removed with piranha ($H_2SO_4$: $H_2O_2$=3:1 by volume). The wafer was then placed in a home-made Teflon® cell for electrochemical etching. The nanopores were formed in a mixture of hydrofluoric acid (HF) and Ethanol (1:3 v/v) with a current density of 16 mA/cm$^2$ applied for 105 second. A higher porosity release layer was formed by applying a current density of 220 mA/cm$^2$ for 6 second. After removing the nitride layer by HF, the particles were released in IPA by exposing the wafer to ultrasonic vibration for 1 minute. The IPA solution containing porous silicon particles was collected and stored.

A drop containing the particles in IPA was directly placed on an aluminum SEM sample stage and dried. The SEM image was measured using a LEO 1530 scanning electron microscope. The acceleration voltage of electron beam was 10 kV, and working distance is about 5 mm. The SEM image in FIG. 10 shows the resulting bowl shaped particles. The particles have about 30 nm pores on the bottom of the bowl and smaller pores on the sides.

EXAMPLE 10

Fabrication of "Large Pore" Silicon Particles with Deep Trenches Etching

FIG. 11 shows an SEM image of fabricated silicon particles with ~1.5 μm deep trench formed by silicon etching. The particles were fabricated as follows.

Heavily doped p++ type (100) wafer with resistivity of 0.005 ohm-cm (Silicon Quest Inc) was used as a substrate. A 100 nm layer of low stress silicon nitride was deposited on the substrate by Low Pressure Chemical Vapor Deposition (LPCVD) System. Standard photolithography was used to pattern the 2 μm circular particle patterns using EVG 620 aligner. The nitride was then selectively removed by reactive ion etching (RIE). The silicon nitride on the back side of the wafer was removed by RIE. The silicon trenches of 1500 nm were etched into silicon on the exposed particle patterns. The photoresist was removed with piranha ($H_2SO_4$:

$H_2O_2$=3:1 by volume). The wafer was then placed in a home-made Teflon® cell for electrochemical etching. The nanopores were formed in a mixture of hydrofluoric acid (HF) and Ethanol (1:3 v/v) by applying a current density of 16 mA/cm² for 105 second. A high porosity release layer was formed by applying a current density of 220 mA/cm² for 6 second. After removing the nitride layer by HF, the particles were released in IPA by exposing the wafer to ultrasonic vibrations for 1 minute. The IPA solution containing porous silicon particles was collected and stored.

A drop containing the particles in IPA was directly placed on an aluminum SEM sample stage and dried. The SEM image was measured using a LEO 1530 scanning electron microscope. The acceleration voltage of electron beam is 10 kV, and working distance is about 5 mm. The SEM image in FIG. 11 shows the resulting bullet shaped particles. The tip 1101 of the bullet has pores of about 30 nm, while the body 1102 of the bullet has smaller pores.

EXAMPLE 11

Fabrication of "Large Pore" Silicon Particles with a Nucleation Layer Removed by RIE FIG. 12 shows SEM cross-section images of fabricated 3.2 μm silicon particles with 500 nm silicon trench etching and: left: with nucleation layer; right: nucleation layer removed by RIE. The particles were fabricated as follows. Heavily doped p++ type (100) wafer with resistivity of 0.005 ohm-cm (Silicon Quest Inc) was used as a substrate. A 100 nm layer of low stress silicon nitride was deposited on the substrate by Low Pressure Chemical Vapor Deposition (LPCVD) System. Standard photolithography was used to pattern the 2 μm circular particle patterns using EVG 620 aligner. The nitride was then selectively removed by reactive ion etching (RIE). The silicon nitride on the back side of the wafer was also removed by RIE. 500 nm silicon trenches were etched into silicon on the exposed particle patterns. The photoresist was removed with piranha ($H_2SO_4$: $H_2O_2$=3:1 by volume). The wafer was then placed in a home-made Teflon® cell for electrochemical etching. The nanopores were formed in a mixture of hydrofluoric acid (HF) and Ethanol (1:3 v/v) by applying a current density of 16 mA/cm₂ for 105 second. A high porosity release layer was formed by applying a current density of 220 mA/cm² for 6 second. Then a short time CF4 RIE was applied to remove the nucleation layer.

For the cross-section study, the particles were not released from the wafer. Instead, after removing the nitride layer by HF, the wafer was cleaved, and mounded on a 45 degree aluminum SEM sample stage. The SEM image was measured using a LEO 1530 scanning electron microscope. The acceleration voltage of electron beam is 10 kV, and working distance is about 5 mm. The SEM image in FIG. 12 compares the cross-section of resulting particles with nucleation layer and particles after removed nucleation layer. The particles with nucleation layer have less than 10 nm pores in the top area 1201, and about 30 nm pores underneath the nucleation layer 1202, while the particles without nucleation layer have about 30 nm pores in both the top area 1203 and the area 1204 beneath the top.

EXAMPLE 12

Fabrication of "Large Pore" Silicon Particles with Two Different Porosity Along Pore Direction FIG. 13 shows an SEM image a porous particle having two different porous regions along pore direction. The particle was fabricated as follows: heavily doped p++ type (100) wafer with resistivity of 0.005 ohm-cm (Silicon Quest Inc) was used as a substrate. A 100 nm layer of low stress silicon nitride was deposited on the substrate by Low Pressure Chemical Vapor Deposition (LPCVD) System. Standard photolithography was used to pattern the 2 circular particle patterns using EVG 620 aligner. The nitride was then selectively removed by reactive ion etching (RIE). The silicon nitride on the back side of the wafer was also removed by RIE. 500 nm silicon trenches are etched into silicon on exposed particle patterns. The photoresist is removed with piranha ($H_2SO_4$:$H_2O_2$=3:1 by volume). The wafer was then placed in a home-made Teflon® cell for electrochemical etching. The nanopores were formed in a mixture of hydrofluoric acid (HF) and Ethanol (1:3 v/v) by applying a current density of 16 mA/cm² for 50 seconds and 37 mA/cm² for 22 seconds.

For the cross-section study, the particles were not released from the wafer. Instead, after removing the nitride layer by HF, the wafer was cleaved, and mounded on a 45 degree aluminum SEM sample stage. The SEM image was measured using a LEO 1530 scanning electron microscope. The acceleration voltage of electron beam is 10 kV, and working distance is about 5 mm. The SEM image in FIG. 13 shows the resulting particles with two different porosity regions 1301 and 1302 along a longitudinal direction besides a nucleation layer 1303. Pores in both regions 1301 and 1302 are perpendicular to the surface. The region 1301 has larger porosity than the region 1302.

EXAMPLE 13

Fabrication of Porous Silicon Films

FIG. 9 shows images of two porous silicon films one with a nucleation layer (FIGS. 9A-B) and one without a nucleation layer (FIG. 9C). The films were fabricated as follows:

Heavily doped p++ type (100) wafer with resistivity of 0.005 ohm-cm (Silicon Quest Inc) was used as a substrate. The wafer was then placed in a home-made Teflon® cell for electrochemical etching. The etching solution is a mixture of hydrofluoric acid (HF) and Ethanol (2:5 v/v). A high density electrical current of 320 mA/cm² was applied for 1 second to remove nucleation layer. The nanopores were formed in with applied current density of 80 mA/cm² for 25 second. Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

Some specific embodiments include the following. A method of fabricating nanoporous silicon particles, comprising: providing a silicon substrate comprising a surface; forming a porous layer on said surface; lithographically patterning a plurality of particles on said substrate, said particles comprising said porous layer; and releasing said particles from the resulting substrate containing patterned porous particles. In some embodiments, lithographic patterning is performed before forming said porous area on said surface.

In some embodiments, releasing said particles comprises mechanically releasing said particles from the lithographically patterned porous particles. In some embodiments, wherein forming said porous layer comprises forming a first porous layer and forming a second porous layer, wherein the porosity of said second layer is greater than that of the first layer. In some embodiments, a protective layer is applied on said substrate. In certain embodiments, the protective layer comprises silicon nitride or a photoresist film. In some embodiments, releasing said particles from said substrate comprises removing the undesired area of said protective layer.

In accordance with some embodiments of an above-described method, patterning comprises defining a predetermined shape for the resulting particles. In some embodiments, said predetermined shape is selected from the group consisting of spherical, square, rectangular, ellipse, disk and semi-spherical.

In accordance with some embodiments, forming of said porous layer comprises tuning the properties of the resulting silicon particles. In certain embodiments, said properties comprise the porosity, pore size and pore profile of said resulting silicon particles. In certain embodiments, said forming of said porous layer comprises electrochemically treating said substrate. In certain embodiments, wherein electrochemically treating said substrate comprises treatment with a solution containing hydrofluoric acid and a surfactant. In certain embodiments, tuning the properties of said silicon particles comprises selecting a concentration of said solution, selecting an electrical current, selecting an etching time, and selecting a doped silicon substrate to provide silicon particles having predetermined properties.

In accordance with some embodiments of an above-described method, said silicon particles comprise an outer surface and a porous interior, and said method further comprises functionalizing at least a portion of said particles. In certain embodiments, said functionalizing comprises modifying at least said outer surface of said particles by application of at least one treatment selected from the group consisting of chemicals, biochemicals, polymers, oxidation, plasma treatment, metal or metal ion coating, CVD film coating, atomic layer deposition, evaporated films, sputtered films and ion implants. In certain embodiments, applying a sacrificial polymer to the porous interior of said particles prior to said functionalizing. In certain embodiments, said functionalizing is performed prior to said releasing of said silicon particles.

Also provided in accordance with embodiments of the present invention is the product of the method of any of the above-described methods. In certain embodiments, the product comprises about 1-3 micron silicon-based nanoporous particles.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments of the invention have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of making porous particles comprising:
providing a substrate having a surface;
forming a first porous layer in the substrate by electrochemical etching using a first current density;
patterning one or more particles on the substrate;
forming in the substrate a second porous layer having a porosity larger than that of the first porous layer by electrochemical etching using a second current density higher than the first current density; and
releasing the patterned one or more particles from the substrate, wherein the releasing comprises breaking the second porous layer, wherein the released one or more particles contain at least a portion of the first porous layer, and wherein a cross section of an individual particle of the one or more particles has a predetermined regular shape.

2. The method of claim 1, wherein the substrate is a semiconductor substrate.

3. The method of claim 1, wherein the substrate is a silicon substrate.

4. The method of claim 1, wherein the first porous layer is formed before the patterning.

5. The method of claim 1, wherein said patterning is performed lithographically.

6. The method of claim 1, wherein a largest dimension of an individual particle of the one or more particles is no more than 5 microns.

7. The method of claim 1, wherein said predetermined regular shape is an oval.

8. The method of claim 3, further comprising forming a trench on the silicon substrate before electrochemical etching the silicon substrate such that said trench is formed in a released individual particle of the one or more particles.

9. The method of claim 8, wherein the trench is positioned on a first porous region of the released individual particle wherein the released individual particle comprises a second porous region in a part of the particle that does not include the trench, and wherein the second porous region differs from the first porous region in at least one property selected from the group consisting of a pore density, a pore size, a pore shape, a pore charge, a pore surface chemistry, and a pore orientation.

10. The method of claim 1, further chemically modifying a surface of the one or more particles.

11. The method of claim 10, wherein said chemically modifying is performed prior to said releasing.

12. The method of claim 11, wherein said chemically modifying modifies a surface of an individual particle of the one or more particles asymmetrically.

13. The method of claim 12, wherein said chemically modifying comprises filling at least a portion of pores of the first porous layer with a sacrificial material.

14. The method of claim 12, wherein the chemically modifying comprises at least one of silanizing, oxidizing and antibody conjugating.

15. The method of claim 1, wherein the first porous layer is a nanoporous layer.

16. The method of claim 1, wherein a pore size in the first porous layer is no more than 100 nm.

17. The method of claim 1, wherein an individual particle of the one or more released particles comprises a first porous region and a second porous region that differs from the first region in at least one property selected from the group consisting of a pore density, a pore size, a pore shape, a pore charge, a pore surface chemistry, and a pore orientation.

18. The method of claim 1, wherein said forming the first porous layer comprises tuning at least one parameter of the first porous layer selected from a thickness, a pore size, porosity, pore orientation and pore shape.

19. The method of claim 1, wherein said forming the first porous layer comprises forming pores of a predetermined profile in said first porous layer.

20. The method of claim 1, wherein said releasing comprises exposing the substrate to an ultrasound.

21. The method of claim 1, further comprising depositing a protective layer on the surface of the substrate.

22. A method of making porous particles comprising:
providing a substrate having a surface;
forming a first porous layer in the substrate by electrochemical etching using a first current density;
patterning one or more particles on the substrate, wherein the first porous layer is formed before the patterning;
forming in the substrate a second porous layer having a porosity larger than that of the first porous layer by electrochemical etching using a second current density higher than the first current density; and
releasing the patterned one or more particles from the substrate, wherein the releasing comprises breaking the second porous layer, and wherein the released one or more particles contain at least a portion of the first porous layer.

23. A method of making porous particles comprising:
providing a substrate having a surface;
forming a first porous layer in the substrate by electrochemical etching using a first current density, wherein said forming the first porous layer comprises forming pores of a predetermined profile in said first porous layer;
patterning one or more particles on the substrate;
forming in the substrate a second porous layer having a porosity larger than that of the first porous layer by electrochemical etching using a second current density higher than the first current density; and
releasing the patterned one or more particles from the substrate, wherein the releasing comprises breaking the second porous layer, and wherein the released one or more particles contain at least a portion of the first porous layer.

24. A method of making porous particles comprising:
providing a substrate having a surface;
forming a first porous layer in the substrate by electrochemical etching using a first current density;
patterning one or more particles on the substrate;
forming in the substrate a second porous layer having a porosity larger than that of the first porous layer by electrochemical etching using a second current density higher than the first current density; and
releasing the patterned one or more particles from the substrate, wherein the releasing comprises breaking the second porous layer, wherein the released one or more particles contain at least a portion of the first porous layer, and wherein a pore size in the first porous layer is no more than 100 nm.

* * * * *

UNITED STATES PATENT AND TRADEMARK OFFICE
CERTIFICATE OF CORRECTION

PATENT NO. : 10,253,424 B2  
APPLICATION NO. : 14/538065  
DATED : April 9, 2019  
INVENTOR(S) : Mauro Ferrari, Xuewu Liu and Ming-Cheng Cheng Page 1 of 1

It is certified that error appears in the above-identified patent and that said Letters Patent is hereby corrected as shown below:

In the Specification

Column 1, Lines 20-24 replace the Government Support Clause with:
--This invention was made with government support under grant numbers CA062349, AI056318, and CA097391 awarded by the National Institutes of Health, and under grant number BES0124897 awarded by the National Science Foundation. The government has certain rights in the invention.--

Signed and Sealed this  
Thirteenth Day of October, 2020

Andrei Iancu  
*Director of the United States Patent and Trademark Office*